United States Patent
Isobe et al.

(10) Patent No.: US 11,718,592 B2
(45) Date of Patent: *Aug. 8, 2023

(54) OXADIAZOLE DERIVATIVE

(71) Applicant: Sumitomo Pharma Co., Ltd., Osaka (JP)

(72) Inventors: Yoshiaki Isobe, Osaka (JP); Tomoyuki Tanaka, Osaka (JP); Hirotaka Miyachi, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/932,871

(22) Filed: Sep. 16, 2022

(65) Prior Publication Data
US 2023/0092498 A1 Mar. 23, 2023

Related U.S. Application Data

(63) Continuation of application No. 17/905,847, filed as application No. PCT/JP2021/010628 on Mar. 16, 2021.

(30) Foreign Application Priority Data

Mar. 17, 2020 (JP) .................................. 2020-046138

(51) Int. Cl.
| | |
|---|---|
| *C07D 271/06* | (2006.01) |
| *C07D 271/10* | (2006.01) |
| *C07D 413/04* | (2006.01) |
| *A61P 25/12* | (2006.01) |
| *A61P 25/24* | (2006.01) |
| *A61P 25/10* | (2006.01) |
| *A61P 25/08* | (2006.01) |

(52) U.S. Cl.
CPC ............ *C07D 271/06* (2013.01); *A61P 25/08* (2018.01); *A61P 25/10* (2018.01); *A61P 25/12* (2018.01); *A61P 25/24* (2018.01); *C07D 271/10* (2013.01); *C07D 413/04* (2013.01)

(58) Field of Classification Search
CPC .. C07D 271/06; C07D 271/10; C07D 413/04; A61P 25/08; A61P 25/10; A61P 25/12; A61P 25/24

See application file for complete search history.

(56) References Cited

U.S. PATENT DOCUMENTS

2014/0275006 A1 9/2014 Yoshinaga et al.

FOREIGN PATENT DOCUMENTS

| JP | 2014-525444 A | 9/2014 |
|---|---|---|
| JP | 2014-224108 A | 12/2014 |
| JP | 2018-507886 A | 3/2018 |
| WO | WO 2006/138512 A2 | 12/2006 |
| WO | WO2008076356 * | 6/2008 ............ A01N 43/82 |
| WO | WO 2010/017132 A1 | 2/2010 |
| WO | WO 2013/033070 A1 | 3/2013 |
| WO | WO 2013/062027 A1 | 5/2013 |
| WO | WO 2014/072957 A1 | 5/2014 |
| WO | WO 2015/161014 A1 | 10/2015 |
| WO | WO 2016/145046 A1 | 9/2016 |

OTHER PUBLICATIONS

International Search Report dated May 25, 2021 in PCT/JP2021/010628 filed Mar. 16, 2021, 7 pages.
Robert S. Fisher, et al., "Operational classification of seizure types by the International League Against Epilepsy: Position Paper of the ILAE Commission for Classification and Terminology", Epilepsia, 58(4), 2017, pp. 522-530.
Anne T. Berg, et al., "Revised terminology and concepts for organization of seizures and epilepsies: Report of the ILAE Commission on Classification and Terminology", Epilepsia, 51(4), 2010, pp. 676-685.
Bettina Schmitz, "Depression and Mania in Patients with Epilepsy", Epilepsia, 46 (Suppl. 4), 2005, pp. 45-49.
CAS Registry No. 2372839-85-3, File Registry [online], Sep. 3, 2019, 1 page.
CAS Registry No. 2372841-01-3, File Registry [online], Sep. 3, 2019, 1 page.
CAS Registry No. 2391021-52-4, File Registry [online], Dec. 15, 2019, 1 page.
CAS Registry No. 2393258-12-1, File Registry [online], Dec. 18, 2019, 1 page.
CAS Registry No. 2395139-54-3, File Registry [online], Dec. 20, 2019, 1 page.
CAS Registry No. 2395140-09-5, File Registry [online], Dec. 20, 2019, 1 page.
CAS Registry No. 2398023-07-7, File Registry [online], Jan. 1, 2020, 2 pages.
CAS Registry No. 2399808-57-0, File Registry [online], Jan. 5, 2020, 1 page.

(Continued)

*Primary Examiner* — Robert H Havlin
(74) *Attorney, Agent, or Firm* — Oblon, McClelland, Maier & Neustadt, L.L.P.

(57) ABSTRACT

The present invention relates to a compound of formula (1) wherein $Q^1$ is halogen atom, $Q^2$ is hydrogen atom, etc., X, Y, and Z are nitrogen atom or oxygen atom, and $R^1$ has a given structure, or a pharmaceutically acceptable salt thereof, and a medicament comprising the compound for treating and/or preventing a disease such as epilepsy.

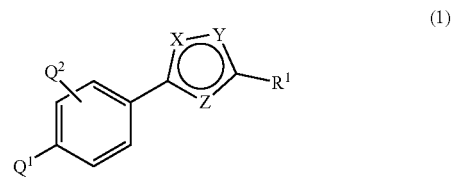

(1)

30 Claims, No Drawings

(56) References Cited

OTHER PUBLICATIONS

CAS Registry No. 2429734-82-5, File Registry [online], Jun. 19, 2020, 1 page.
CAS Registry No. 2429736-73-0, File Registry [online], Jun. 19, 2020, 1 page.
CAS Registry No. 2433152-21-5, File Registry [online], Jun. 24, 2020, 1 page.
CAS Registry No. 2433544-91-1, File Registry [online], Jun. 24, 2020, 1 page.
CAS Registry No. 2434477-84-4, File Registry [online], Jun. 26, 2020, 1 page.
CAS Registry No. 2454150-20-8, File Registry [online], Aug. 6, 2020, 1 page.
CAS Registry No. 2456305-65-8, File Registry [online], Aug. 12, 2020, 1 page.
CAS Registry No. 2459729-04-3, File Registry [online], Aug. 19, 2020, 1 page.
CAS Registry No. 2459865-29-1, File Registry [online], Aug. 20, 2020, 1 page.
CAS Registry No. 2461806-70-0, File Registry [online], Aug. 26, 2020, 1 page.
CAS Registry No. 2461981-80-4, File Registry [online], Aug. 27, 2020, 1 page.
CAS Registry No. 2462268-37-5, File Registry [online], Aug. 27, 2020, 1 page.
CAS Registry No. 2463630-55-7, File Registry [online], Aug. 27, 2020, 1 page.
CAS Registry No. 2463706-64-9, File Registry [online], Aug. 27, 2020, 1 page.
CAS Registry No. 2463745-70-0, File Registry [online], Aug. 27, 2020, 1 page.
CAS Registry No. 2463903-64-0, File Registry [online], Aug. 27, 2020, 1 page.
CAS Registry No. 2464072-27-1, File Registry [online], Aug. 27, 2020, 2 pages.
CAS Registry No. 2464618-52-6, File Registry [online], Aug. 28, 2020, 1 page.
CAS Registry No. 2464868-57-1, File Registry [online], Aug. 27, 2020, 1 page.
CAS Registry No. 2465199-54-4, File Registry [online], Aug. 27, 2020, 1 page.
CAS Registry No. 2465276-05-3, File Registry [online], Aug. 27, 2020, 1 page.
CAS Registry No. 2465699-93-6, File Registry [online], Aug. 28, 2020, 2 pages.
CAS Registry No. 2465711-86-6, File Registry [online], Aug. 28, 2020, 1 page.
CAS Registry No. 2465992-77-0, File Registry [online], Aug. 28, 2020, 1 page.
CAS Registry No. 2466368-39-6, File Registry [online], Aug. 28, 2020, 1 page.
CAS Registry No. 2466822-24-0, File Registry [online], Aug. 28, 2020, 1 page.
CAS Registry No. 2467263-41-6, File Registry [online], Aug. 28, 2020, 1 page.
CAS Registry No. 2467934-22-9, File Registry [online], Aug. 28, 2020, 1 page.
CAS Registry No. 2470141-73-0, File Registry [online], Sep. 2, 2020, 1 page.
International Preliminary Report on Patentability and Written Opinion dated Sep. 20, 2022 in PCT/JP2021/010628 (submitting English translation only), 5 pages.

\* cited by examiner

OXADIAZOLE DERIVATIVE

CROSS-REFERENCE TO RELATED APPLICATIONS

The present application is a continuation of and claims the benefit of priority to U.S. application Ser. No. 17/905,847, filed Sep. 8, 2022, which is a 35 U.S.C. § 371 national stage patent application of International patent application PCT/JP2021/010628, filed on Mar. 16, 2021, which is based on and claims the benefits of priority to Japanese Application No. 2020-046138, filed on Mar. 17, 2020. The entire contents of all of the above applications are incorporated herein by reference.

TECHNICAL FIELD

The present invention relates to an oxadiazole derivative or a pharmaceutically acceptable salt thereof which is useful as a medicament, and a pharmaceutical composition or a medicament for treating and/or preventing epilepsy and/or depressive syndrome, etc., comprising the derivative as an active ingredient.

BACKGROUND ART

Epilepsy is a chronic disease caused by the hyperexcitability of cerebral neuron, whose symptom is that unusual somatic symptom, or the change of motion, consciousness, or sensation suddenly comes up repeatedly. The epileptic seizure type is classified by the International League Against Epilepsy (ILAE) into generalized seizure, focal seizure, and an unknown seizure, wherein generalized seizure is further classified into tonic seizure, clonic seizure, absence seizure, myoclonic seizure, atonic seizure, etc. (Non-patent Literature 1). The etiologies for epilepsy are roughly categorized into genetic, structural/metabolic, and unknown. In addition, epilepsy is classified into various disease types and syndromes based on the characters such as electroencephalogram/clinical symptom, age of onset, and disease pathogenesis. It includes, for example, West syndrome and Dravet syndrome which occur during infancy, Lennox-Gastaut syndrome and autosomal dominant nocturnal frontal lobe epilepsy (ADNFLE) which occur during childhood, mesial temporal lobe epilepsy associated with hippocampal sclerosis which is a definitely identified symptom, Rasmussen's syndrome, and many others (Non-patent Literature 2). Since the 1990s, international collaborative researches of, especially, molecular pathology of epilepsy have been developed, and many of causative genes have been identified until now. These genes include ion channel such as Na, K, Ca, Cl, GABA-A, and ACh, and it is guessed that epilepsy is caused by ion homeostasis abnormality which is one of the causes.

Epilepsy is a severe disease which can affect prognosis, and it is known that about 1% of the world's population suffer from epilepsy. The treatment of these epileptic seizures has been carried out mainly by drug therapy. Despite the fact that various antiepileptic drugs have been prescribed for many years, one of three examples in the treatment of epilepsy is refractory and resistant to multidrug therapy with existing drugs. In addition, existing drugs for epilepsy have dose-related side effects to nervous system such as excessive sleepiness, wobble, cognitive impairment, and psychiatric symptom; severe idiosyncratic side effects such as Stevens-Johnson syndrome though in rare cases; teratogenic risks; and drug-interaction risks such as loss of drug-efficacy and increase of side effects. Furthermore, patients suffering from epilepsy have high complication risk with psychiatric symptom such as depression, anxiety, and cognitive impairment (Non-patent Literature 3). However, existing drugs for epilepsy have no therapeutic effect to such complicated psychiatric symptoms. Thus, it has been strongly desired to develop a new antiepileptic drug having multiple properties, for example, a high efficacy for refractory epilepsy, a superior profile on pharmacokinetics and safety, and an efficacy for both epilepsy and complicated psychiatric symptoms.

Epilepsy causes seizure by hyperexcitability of brain neuron, which is caused when excitatory neuron strongly acts, or inhibitory neuron weakens, i.e., the cause is thought to be abnormality of the balance between excitation (E) and inhibition (I) (E/I balance). Besides epilepsy, some diseases that are caused by abnormality of E/I balance are known. Drugs that enhance the GABAergic system by activation of inhibitory neurons exhibit some therapeutic effects for anxiety disorder, obsessive-compulsive disorder, and REM sleep behavior disorder associated with Parkinson's disease/dementia with Lewy bodies. And, it is known that the abnormality of E/I balance is also related to neuropathic pain, developmental disorder, autism, bipolar disorder, schizophrenia, Alzheimer's disease and the other dementia, amyotrophic lateral sclerosis, Parkinson's disease, etc. In fact, some of antiepileptic drugs which can improve the abnormality of E/I balance have been broadly used in the treatment of these diseases. However, these drugs have limitations of the efficaciousness for these diseases other than epilepsy, and also have problems of side effects and pharmacokinetics. Thus, if a new antiepileptic drug having new profiles of efficacies and side effect is developed, the drug may have a possibility of applying to many psychiatric diseases or neurological diseases, and the development thereof is meaningful.

Patent Literature 1 discloses oxadiazoles which have an effect as sweet taste modifiers, but whose structures are different from that of the compound of formula (1) which is shown below.

PRIOR ART

Patent Reference

[Patent Literature 1] WO 2006/138512

Non-Patent Reference

[Non-patent Literature 1] Robert S. Fisher et al. Epilepsia, (2017), 58(4), 522-530
[Non-patent Literature 2] Anne T. Berg et al. Epilepsia, (2010) 51(4), 676-85
[Non-patent Literature 3] Schmitz B. Epilepsia, (2005) 46 (Suppl. 4), 45-49

SUMMARY OF INVENTION

Technical Problem

The purpose of the present invention may be to provide a compound useful as an antiepileptic drug.

Solution to Problem

The present inventors have extensively studied to reach the above purpose, and then have found that a compound of the following formula (1) has a potent anticonvulsant action, i.e., the present inventors have found out that the compound has antiepileptic action as well as the potentiating effect on GABA(A) receptor. Based upon the findings, the present invention has been achieved. According to the present invention, the oxadiazole derivative of the following formula (1) (hereinafter referred to as "the present compound", as appropriate) is provided.

Accordingly, the present invention is described as follows:

(Item 1)

A compound of formula (1):

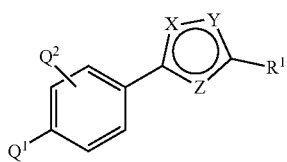

(1)

or a pharmaceutically acceptable salt thereof, wherein
$Q^1$ is halogen,
$Q^2$ is hydrogen, halogen, cyano, $C_{1-3}$ alkyl (which may be substituted with 1 to 3 substituents selected independently from the group consisting of halogen, hydroxy, $C_{3-6}$ cycloalkyl, and $C_{1-3}$ alkoxy), or $C_{1-3}$ alkoxy (which may be substituted with 1 to 3 substituents selected independently from the group consisting of halogen, hydroxy, $C_{3-6}$ cycloalkyl, and $C_{1-3}$ alkoxy),
X, Y, and Z are the same or different and are nitrogen atom or oxygen atom, provided that the ring containing X, Y, and Z is a heteroaryl wherein any two of X, Y, and Z are nitrogen atom and the other is oxygen atom,
$R^1$ is any one of the following formulae (2) to (4):

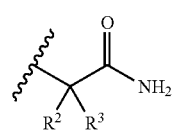

(2)

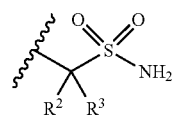

(3)

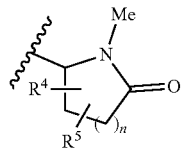

(4)

$R^2$ and $R^3$ are the same or different and are $C_{1-6}$ alkyl (which may be substituted with 1 to 3 substituents selected independently from the group consisting of halogen, hydroxy, $C_{3-6}$ cycloalkyl, and $C_{1-3}$ alkoxy) or $C_{3-6}$ cycloalkyl (which may be substituted with 1 to 3 substituents selected independently from the group consisting of halogen, hydroxy, $C_{1-3}$ alkyl, and $C_{1-3}$ alkoxy); or $R^2$ and $R^3$ may be taken together with the carbon atom to which they are attached to form $C_{3-6}$ cycloalkyl (which may be substituted with 1 to 3 substituents selected independently from the group consisting of halogen, hydroxy, $C_{1-3}$ alkyl, and $C_{1-3}$ alkoxy), or $C_{4-6}$ saturated hetero ring containing one or two heteroatoms selected independently from nitrogen atom and oxygen atom (said saturated hetero ring may be substituted with 1 to 3 substituents selected independently from the group consisting of halogen, hydroxy, $C_{1-3}$ alkyl, and $C_{1-3}$ alkoxy), $R^4$ and $R^5$ are the same or different and are hydrogen, halogen, hydroxy, $C_{1-6}$ alkyl (which may be substituted with 1 to 3 substituents selected independently from the group consisting of halogen, hydroxy, $C_{3-6}$ cycloalkyl, and $C_{1-3}$ alkoxy), or $C_{3-6}$ cycloalkyl (which may be substituted with 1 to 3 substituents selected independently from the group consisting of halogen, hydroxy, $C_{1-3}$ alkyl, and $C_{1-3}$ alkoxy); or when $R^4$ and R are attached to the same carbon atom or to two adjacent carbon atoms respectively, $R^4$ and $R^5$ may be taken together with the carbon atom(s) to which they are attached to form $C_{3-6}$ cycloalkyl (which may be substituted with 1 to 3 substituents selected independently from the group consisting of halogen, hydroxy, $C_{1-3}$ alkyl, and $C_{1-3}$ alkoxy), or $C_{4-6}$ saturated hetero ring containing one or two heteroatoms selected independently from nitrogen atom and oxygen atom (said saturated hetero ring may be substituted with 1 to 3 substituents selected independently from the group consisting of halogen, hydroxy, $C_{1-3}$ alkyl, and $C_{1-3}$ alkoxy), and n is an integer of 0 to 2.

(Item 2)

The compound of Item 1 or a pharmaceutically acceptable salt thereof, wherein
$R^2$ and $R^3$ are the same or different and are $C_{1-3}$ alkyl (which may be substituted with 1 to 3 substituents selected independently from the group consisting of fluorine, hydroxy, and $C_{1-3}$ alkoxy); or $R^2$ and $R^3$ may be taken together with the carbon atom to which they are attached to form $C_{3-6}$ cycloalkyl (which may be substituted with 1 to 3 substituents selected independently from the group consisting of fluorine, hydroxy, $C_{1-3}$ alkyl, and $C_{1-3}$ alkoxy), or $C_{4-6}$ saturated hetero ring containing one or two heteroatoms selected independently from nitrogen atom and oxygen atom (said saturated hetero ring may be substituted with 1 to 3 substituents selected independently from the group consisting of fluorine, hydroxy, $C_{1-3}$ alkyl, and $C_{1-3}$ alkoxy).

(Item 3)

The compound of Item 2 or a pharmaceutically acceptable salt thereof, wherein
$R^2$ and $R^3$ are the same or different and are $C_{1-3}$ alkyl which may be substituted with fluorine; or $R^2$ and $R^3$ may be taken together with the carbon atom to which they are attached to form $C_{3-6}$ cycloalkyl (which may be substituted with fluorine), or $C_{4-6}$ saturated hetero ring containing one or two heteroatoms selected independently from nitrogen atom and oxygen atom (said saturated hetero ring may be substituted with fluorine).

(Item 4)

The compound of any one of Items 1 to 3 or a pharmaceutically acceptable salt thereof, wherein
$R^4$ and $R^5$ are the same or different and are hydrogen, fluorine, hydroxy, $C_{1-3}$ alkyl (which may be substituted with 1 to 3 substituents selected independently from the group consisting of fluorine, hydroxy, and $C_{1-3}$ alkoxy), or $C_{3-6}$ cycloalkyl (which may be substituted with 1 to 3 substituents selected independently from the group consisting of fluorine, hydroxy, $C_{1-3}$ alkyl, and $C_{1-3}$ alkoxy); or when $R^4$ and $R^5$ are attached to the same carbon atom or to two adjacent carbon atoms respectively, $R^4$ and $R^5$ may be taken together with the carbon atom(s) to which they are attached to form $C_{3-6}$ cycloalkyl (which may be substituted with 1 to 3 substituents selected independently from the group consisting of fluorine, hydroxy, $C_{1-3}$ alkyl, and $C_{1-3}$ alkoxy), or $C_{4-6}$ saturated hetero ring containing one or two heteroatoms selected independently from nitrogen atom and oxygen atom (said saturated hetero ring may be substituted with 1 to 3 substituents selected independently from the group consisting of fluorine, hydroxy, $C_{1-3}$ alkyl, and $C_{1-3}$ alkoxy).

(Item 5)

The compound of Item 4 or a pharmaceutically acceptable salt thereof, wherein $R^4$ and $R^5$ are the same or different and are hydrogen, fluorine, hydroxy, $C_{1-3}$ alkyl (which may be substituted with fluorine), or $C_{3-6}$ cycloalkyl (which may be substituted with fluorine); or when $R^4$ and $R^5$ are attached to the same carbon atom or to two adjacent carbon atoms respectively, $R^4$ and $R^5$ may be taken together with the carbon atom(s) to which they are attached to form $C_{3-6}$ cycloalkyl which may be substituted with 1 to 3 substituents selected independently from the group consisting of fluorine and $C_{1-3}$ alkyl.

(Item 6)

The compound of any one of Items 1 to 5 or a pharmaceutically acceptable salt thereof, wherein $Q^1$ is fluorine, chlorine, or bromine, and $Q^2$ is hydrogen, fluorine, chlorine, bromine, cyano, $C_{1-3}$ alkyl (which may be substituted with fluorine), or $C_{1-3}$ alkoxy (which may be substituted with fluorine).

(Item 7)

The compound of any one of Items 1 to 6 or a pharmaceutically acceptable salt thereof, wherein the ring containing X, Y, and Z is the following (5a), (5b), or (5c).

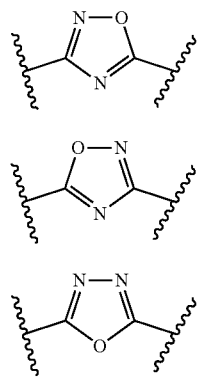

(5a)

(5b)

(5c)

(Item 8)

The compound of Item 7 or a pharmaceutically acceptable salt thereof, wherein the ring containing X, Y, and Z is the following (5a) or (5b).

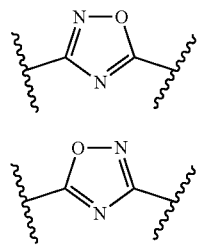

(5a)

(5b)

(Item 9)

The compound of any one of Items 1 to 3 and 6 to 8 or a pharmaceutically acceptable salt thereof, wherein $R^1$ is the following (2) or (3).

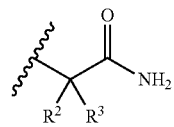

(2)

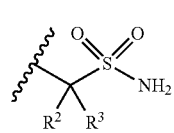

(3)

(Item 10)

The compound of any one of Items 1 and 4 to 8 or a pharmaceutically acceptable salt thereof, wherein $R^1$ is the following (4).

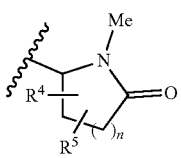

(4)

(Item 11)

The compound of Item 1 or a pharmaceutically acceptable salt thereof, which is selected from the following compounds:

2-[3-(4-fluorophenyl)-1,2,4-oxadiazol-5-yl]-2-methylpropanamide (Example 1),

2-[3-(4-chlorophenyl)-1,2,4-oxadiazol-5-yl]-2-methylpropanamide (Example 2),

2-[3-(4-bromophenyl)-1,2,4-oxadiazol-5-yl]-2-methylpropanamide (Example 3),

1-[3-(4-fluorophenyl)-1,2,4-oxadiazol-5-yl]cyclopropane-1-carboxamide (Example 4), 1-[3-(4-chlorophenyl)-1,2,4-oxadiazol-5-yl]cyclopropane-1-carboxamide (Example 5), 1-[3-(4-chlorophenyl)-1,2,4-oxadiazol-5-yl]-3-fluorocyclobutane-1-carboxamide (Example 6), 1-[3-(4-chlorophenyl)-1,2,4-oxadiazol-5-yl]-3,3-difluorocyclobutane-1-carboxamide (Example 7), 1-[3-(4-chlorophenyl)-1,2,4-oxadiazol-5-yl]cyclobutane-1-carboxamide (Example 8), 1-[3-(4-chlorophenyl)-1,2,4-oxadiazol-5-yl]cyclopentane-1-carboxamide (Example 9), 4-[3-(4-fluorophenyl)-1,2,4-oxadiazol-5-yl]tetrahydro-2H-pyran-4-carboxamide (Example 10), 2-[3-(4-chlorophenyl)-1,2,4-oxadiazol-5-yl]-2-ethylbutanamide (Example 11), 2-[5-(4-fluorophenyl)-1,2,4-oxadiazol-3-yl]-2-methylpropanamide (Example 12), 2-[5-(4-chlorophenyl)-1,2,4-oxadiazol-3-yl]-2-methylpropanamide (Example 13), 2-[5-(4-bromophenyl)-1,2,4-oxadiazol-3-yl]-2-methylpropanamide (Example 14), 2-[5-(4-chlorophenyl)-1,3,4-oxadiazol-2-yl]-2-methylpropanamide (Example 15), 2-[5-(4-bromophenyl)-1,3,4-oxadiazol-2-yl]-2-methylpropanamide (Example 16), 2-[3-(4-fluorophenyl)-1,2,4-oxadiazol-5-yl]propane-2-sulfonamide (Example 17),
2-[3-(4-chlorophenyl)-1,2,4-oxadiazol-5-yl]propane-2-sulfonamide (Example 18),
2-[3-(4-bromophenyl)-1,2,4-oxadiazol-5-yl]propane-2-sulfonamide (Example 19),
2-[5-(4-chlorophenyl)-1,2,4-oxadiazol-3-yl]propane-2-sulfonamide (Example 20),
2-[5-(4-bromophenyl)-1,2,4-oxadiazol-3-yl]propane-2-sulfonamide (Example 21),
2-[5-(4-fluorophenyl)-1,3,4-oxadiazol-2-yl]propane-2-sulfonamide (Example 22),
2-[5-(4-chlorophenyl)-1,3,4-oxadiazol-2-yl]propane-2-sulfonamide (Example 23),
2-[5-(4-bromophenyl)-1,3,4-oxadiazol-2-yl]propane-2-sulfonamide (Example 24),
5-[3-(4-fluorophenyl)-1,2,4-oxadiazol-5-yl]-1-methylpyrrolidin-2-one (Example 25),
5-[3-(2,4-difluorophenyl)-1,2,4-oxadiazol-5-yl]-1-methylpyrrolidin-2-one (Example 26),
5-[3-(3,4-difluorophenyl)-1,2,4-oxadiazol-5-yl]-1-methylpyrrolidin-2-one (Example 27),
5-[3-(4-fluorophenyl)-1,2,4-oxadiazol-5-yl]-1,5-dimethylpyrrolidin-2-one (Example 28),
5-[3-(4-chlorophenyl)-1,2,4-oxadiazol-5-yl]-1-methylpyrrolidin-2-one (Example 29),
5-[3-(4-bromophenyl)-1,2,4-oxadiazol-5-yl]-1-methylpyrrolidin-2-one (Example 30),
(S)-5-[3-(4-fluorophenyl)-1,2,4-oxadiazol-5-yl]-1-methylpyrrolidin-2-one (Example 31), and
(R)-5-[3-(4-fluorophenyl)-1,2,4-oxadiazol-5-yl]-1-methylpyrrolidin-2-one (Example 32).

(Item 12)
The compound of Item 1 or a pharmaceutically acceptable salt thereof, which is selected from the following compounds:
2-[3-(4-chlorophenyl)-1,2,4-oxadiazol-5-yl]-2-methylpropanamide (Example 2),
2-[3-(4-bromophenyl)-1,2,4-oxadiazol-5-yl]-2-methylpropanamide (Example 3),
2-[5-(4-chlorophenyl)-1,2,4-oxadiazol-3-yl]-2-methylpropanamide (Example 13),
2-[5-(4-chlorophenyl)-1,2,4-oxadiazol-3-yl]propane-2-sulfonamide (Example 20),
5-[3-(4-fluorophenyl)-1,2,4-oxadiazol-5-yl]-1-methylpyrrolidin-2-one (Example 25),
5-[3-(4-chlorophenyl)-1,2,4-oxadiazol-5-yl]-1-methylpyrrolidin-2-one (Example 29),
(S)-5-[3-(4-fluorophenyl)-1,2,4-oxadiazol-5-yl]-1-methylpyrrolidin-2-one (Example 31), and
(R)-5-[3-(4-fluorophenyl)-1,2,4-oxadiazol-5-yl]-1-methylpyrrolidin-2-one (Example 32).

(Item 13)
A pharmaceutical composition comprising the compound of any one of Items 1 to 12 or a pharmaceutically acceptable salt thereof.

(Item 14)
A medicament for treating and/or preventing neurological disease or psychiatric disease, comprising the compound of any one of Items 1 to 12 or a pharmaceutically acceptable salt thereof as an active ingredient.

(Item 15)
A medicament for treating and/or preventing a disease in which excitation (E) is increased and/or inhibition (I) is decreased in E/I balance, comprising the compound of any one of Items 1 to 12 or a pharmaceutically acceptable salt thereof as an active ingredient.

(Item 16)
A medicament for treating and/or preventing diseases associated with hypofunction of GABAergic system, comprising the compound of any one of Items 1 to 12 or a pharmaceutically acceptable salt thereof as an active ingredient.

(Item 17)
The medicament of Item 16, wherein the diseases associated with hypofunction of GABAergic system are neurological disease or psychiatric disease.

(Item 18)
The medicament of Item 14 or 17, wherein the neurological disease or psychiatric disease is epileptic seizure (generalized seizure including tonic seizure, clonic seizure, absence seizure, myoclonic seizure, and atonic seizure, focal seizure, an unknown seizure), status epilepticus, West syndrome, Dravet syndrome, Lennox-Gastaut syndrome, autosomal dominant nocturnal frontal lobe epilepsy (ADNFLE), mesial temporal lobe epilepsy associated with hippocampal sclerosis which is a definitely identified symptom, Rasmussen syndrome, depressive symptom accompanying or unaccompanying epilepsy, anxiety disorder, obsessive-compulsive disorder, REM sleep behavior disorder associated with Parkinson's disease/dementia with Lewy bodies, neuropathic pain, developmental disorder, autism, bipolar disorder, schizophrenia, Alzheimer's disease and the other dementia, amyotrophic lateral sclerosis, or Parkinson's disease.

(Item 19)
The medicament of Item 14 or 17, wherein the neurological disease or psychiatric disease is epilepsy, neuropathic pain, neurodevelopmental disorders, bipolar disorder and its related disorders, schizophrenia spectrum disorder, Alzheimer's disease and the other neurocognitive disorders, amyotrophic lateral sclerosis, Parkinson's disease, depressive syndrome, anxiety disorders, obsessive-compulsive disorder, trauma- and stressor-related disorders, sleep-wake disorders, and/or REM sleep behavior disorder associated with Parkinson's disease/dementia with Lewy bodies.

(Item 20)
A method for treating and/or preventing diseases associated with hypofunction of GABAergic system, comprising administering a therapeutically effective amount of the compound of any one of Items 1 to 12 or a pharmaceutically acceptable salt thereof to a patient in need thereof.

(Item 21)
Use of the compound of any one of Items 1 to 12 or a pharmaceutically acceptable salt thereof, in the manufacture of a medicament for treating and/or preventing diseases associated with hypofunction of GABAergic system.

(Item 22)
The compound of any one of Items 1 to 12 or a pharmaceutically acceptable salt thereof for use in treating and/or preventing diseases associated with hypofunction of GABAergic system.

(Item 23)
A medicament for treating and/or preventing epilepsy, comprising the compound of any one of Items 1 to 12, or a pharmaceutically acceptable salt thereof as an active ingredient.

(Item 24)
The medicament of Item 23, wherein the epilepsy is epileptic seizure (tonic seizure, clonic seizure, absence seizure, myoclonic seizure, generalized seizure including atonic seizure, focal seizure, an unknown seizure), status epilepticus, West syndrome, Dravet syndrome, Lennox-Gastaut syndrome, autosomal dominant nocturnal frontal lobe epilepsy (ADNFLE), mesial temporal lobe epilepsy associated with hippocampal sclerosis which is a definitely identified symptom, or Rasmussen syndrome.

(Item 25)
A method for treating and/or preventing epilepsy, comprising administering a therapeutically effective amount of the compound of any one of Items 1 to 12 or a pharmaceutically acceptable salt thereof to a patient in need thereof.

(Item 26)
Use of the compound of any one of Items 1 to 12 or a pharmaceutically acceptable salt thereof, in the manufacture of a medicament for treating and/or preventing epilepsy.

(Item 27)
The compound of any one of Items 1 to 12 or a pharmaceutically acceptable salt thereof for use in treating and/or preventing epilepsy.

(Item 28)
A pharmaceutical combination comprising the compound of any one of Items 1 to 12 or a pharmaceutically acceptable salt thereof, and at least one drug selected from drugs classified into antiepileptic drug, antidepressant drug, or antipsychotic drug.

(Item 29)
A medicament for treating diseases associated with hypofunction of GABAergic system, comprising the compound of any one of Items 1 to 12, or a pharmaceutically acceptable salt thereof, which is used in combination with at least one drug selected from drugs classified into antiepileptic drug, antidepressant drug, or antipsychotic drug.

(Item 30)
A process for preparing Compound (Ic), comprising
a step wherein Compound (IIc1) and Compound (IIc2) are reacted to give Compound (IIc'), and
a step wherein Compound (IIc') is methylated, as shown in the following scheme:

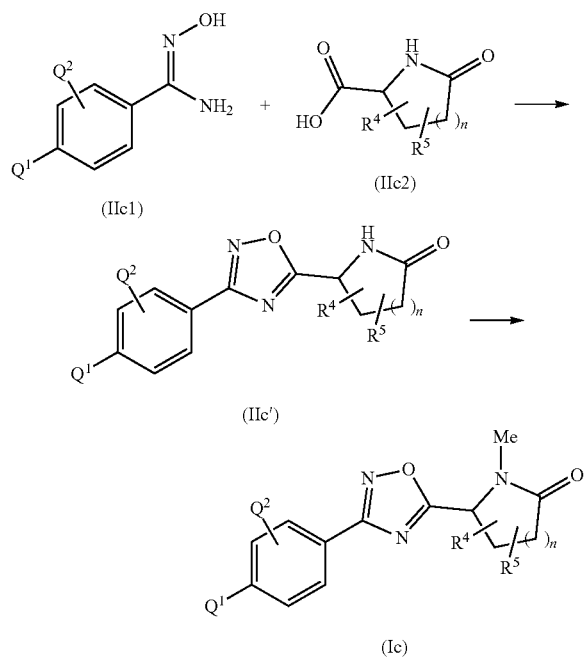

wherein each symbol is as defined above.

(Item 31)
A process for preparing Compound (Ic'), comprising a step wherein Compound (IIc1') and Compound (IIc2') are reacted as shown in the following scheme:

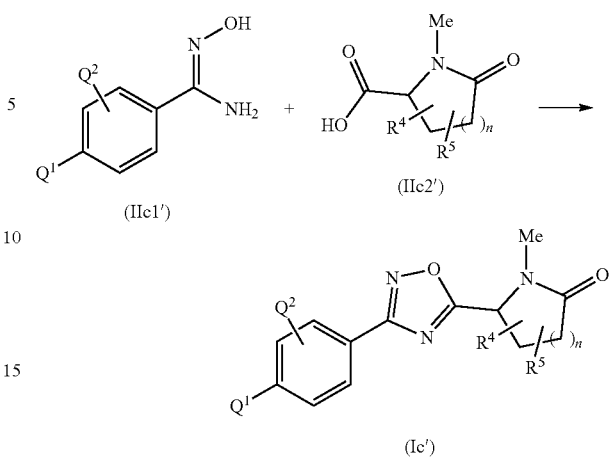

wherein each symbol is as defined above.

Effect of the Invention

The present compounds exhibited a potent anticonvulsant effect for several animal models of seizures caused by the decrease of GABA signal (the model produced by subcutaneous injection of pentetrazol in Test 1, and the mouse model of Dravet Syndrome with febrile seizures in Test 3). The model produced by subcutaneous injection of pentetrazol in Test 1 is an animal model with seizure type which expresses generalized absence seizure or myoclonic seizure, and shows low remission rate against existing antiepileptic drugs. The mouse model of Dravet with febrile seizures in Test 3 is an animal model having the same genetic background as Dravet syndrome which presents treatment-resistant seizures. The effect of existing antiepileptic drugs to the model is very limited. Thus, the present compounds are useful as a medicament for treating and/or preventing epilepsy such as epileptic seizure (tonic seizure, clonic seizure, absence seizure, myoclonic seizure, generalized seizure including atonic seizure, focal seizure, an unknown seizure), status epilepticus, West syndrome, Dravet syndrome, Lennox-Gastaut syndrome, autosomal dominant nocturnal frontal lobe epilepsy (ADNFLE), mesial temporal lobe epilepsy associated with hippocampal sclerosis which is a definitely identified symptom, and Rasmussen syndrome. Among these diseases, West syndrome, Dravet syndrome, and Lennox-Gastaut syndrome are severe diseases which present treatment-resistant seizure and involve developmental delay, etc., thus it is very meaningful to provide a medicament for preventing and/or treating intractable epilepsy including these diseases. The potentiating effect of the present compounds on GABA(A) receptors is exerted in a different mechanism of action from benzodiazepine which is one of existing agonists of GABA (A) receptor, and in fact, the result of Test 5 showed that the present compounds exhibit a positive effect for the depressive symptom in rat forced swimming test to which benzodiazepine does not exhibit the effect. Thus, the present compounds have some effect for depressive symptom accompanying or unaccompanying epilepsy, and have utility which existing antiepileptic drugs do not have. The potentiating effect of the present compounds on GABA(A) receptors is also useful as a medicament for treating and/or preventing anxiety disorder, obsessive-compulsive disorder, REM sleep behavior disorder associated with Parkinson's disease/dementia with Lewy bodies, which can be treated with existing GABA(A) receptor agonists. And, the present compounds are expected to improve the pathological conditions of neuropathic pain, developmental disorder, autism, bipolar disorder, schizophrenia, Alzheimer's disease and the other dementia, amyotrophic lateral sclerosis, and Parkinson's disease, which have underlying reason for the dysfunction of GABAergic system. In addition, the present compounds are also useful as a medicament for preventing and/or treating the other diseases mentioned herein.

In addition, the present compounds have an effect for enhancing inhibition (I) in balance of excitation (E) and inhibition (I) (E/I balance), thus the present compounds may be a medicament for treating and/or preventing neurological disease or psychiatric disease, in particular, a medicament for treating and/or preventing a disease in which excitation (E) is increased and/or inhibition (I) is decreased in E/I balance.

DESCRIPTION OF EMBODIMENTS

Hereinafter, the terms used herein are explained as follows.

Unless otherwise specified, the definition of each substituent group also extends over the case of partially-including the substituent group or the case of the substituent group existing on another substituent group.

The "halogen" includes, for example, fluorine, chlorine, bromine, and iodine. It is preferably fluorine or chlorine, and more preferably fluorine.

The "$C_{1-6}$ alkyl" means straight or branched chain of saturated hydrocarbon group having 1 to 6 carbon atoms, and "$C_6$ alkyl" means alkyl having 6 carbon atoms. The same is applied to the case of the other carbon numbers. The "$C_{1-6}$ alkyl" includes preferably "$C_{1-3}$ alkyl", more preferably "$C_{1-2}$ alkyl". The "$C_{1-3}$ alkyl" includes preferably "$C_{1-2}$ alkyl", more preferably methyl. The "$C_{1-2}$ alkyl" includes, for example, methyl, ethyl, and the like. The "$C_{1-3}$ alkyl" includes, for example, propyl, 1-methylethyl, and the like, besides the examples listed in the said "$C_{1-2}$ alkyl". The "$C_{1-6}$ alkyl" includes, for example, butyl, 1,1-dimethylethyl, 1-methylpropyl, 2-methylpropyl, pentyl, 2-methylbutyl, 3-methylbutyl, 2,2-dimethylpropyl, 1-ethylpropyl, 1,1-dimethylpropyl, 4-methylpentyl, 3-methylpentyl, 2-methylpentyl, 1-methylpentyl, hexyl, and the like, besides the examples listed in the said "$C_{1-3}$ alkyl".

The "$C_{3-6}$ cycloalkyl" means cyclic alkyl having 3 to 6 carbon atoms, which may have a bridged structure. The "$C_{3-6}$ cycloalkyl" includes preferably "$C_{3-5}$ cycloalkyl". The "$C_{3-5}$ cycloalkyl" includes, for example, cyclopropyl, cyclobutyl, cyclopentyl, and the like. The "$C_{3-6}$ cycloalkyl" includes, for example, cyclohexyl and the like, besides the examples listed in the said "$C_{3-5}$ cycloalkyl".

The "$C_{1-3}$ alkoxy" means oxy group substituted with the above "$C_{1-3}$ alkyl". The "$C_{1-3}$ alkoxy" includes preferably "$C_{1-2}$ alkoxy", more preferably "methoxy". The "$C_{1-2}$ alkoxy" includes, for example, methoxy, ethoxy, and the like. The "$C_{1-3}$ alkoxy" includes, for example, propoxy, 1-methylethoxy, and the like, besides the examples listed in the said "$C_{1-2}$ alkoxy".

The "$C_{4-6}$ saturated hetero ring" means a 4- to 6-membered saturated ring that has the same or different and one or more heteroatoms selected from nitrogen atom, oxygen atom, and sulfur atom, which may have a bridged structure. Preferred one thereof is a $C_{4-6}$ saturated hetero ring containing one or two heteroatoms selected independently from nitrogen atom and oxygen atom. The "$C_{4-6}$ saturated hetero ring" includes preferably "$C_{4-5}$ saturated hetero ring". The "$C_{4-5}$ saturated hetero ring" includes, for example, oxetane, azetidine, tetrahydrofuran, pyrrolidine, and the like. The "$C_{4-6}$ saturated hetero ring" includes, for example, tetrahydropyran, piperidine, morpholine, piperazine, and the like, besides the examples listed in the said "$C_{4-5}$ saturated hetero ring".

Preferred $R^1$, $R^2$, $R^3$, $R^4$, $R^5$, X, Y, Z, $Q^1$, $Q^2$, and n are shown below, but the technical scope of the present invention is not limited to the scope of compounds listed below.

In an embodiment, $R^1$ includes the following (2)-(4)

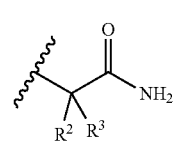

(2)

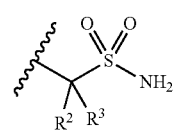

(3)

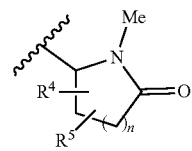

(4)

In another embodiment, $R^1$ includes the following (2) or (3).

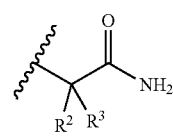

(2)

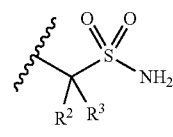

(3)

In another embodiment, $R^1$ includes the following (4).

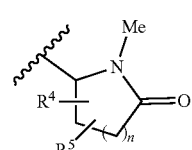

(4)

In a preferred embodiment of $R^2$ and $R^3$, $R^2$ and $R^3$ are the same or different and are (1) $C_{1-3}$ alkyl which may be substituted with 1 to 3 substituents selected independently from the group consisting of fluorine, hydroxy, and $C_{1-3}$ alkoxy; or (2) $R^2$ and $R^3$ are taken together with the carbon atom to which they are attached to form $C_{3-6}$ cycloalkyl which may be substituted with 1 to 3 substituents selected independently from the group consisting of fluorine, hydroxy, $C_{1-3}$ alkyl, and $C_{1-3}$ alkoxy, or (3) $R^2$ and $R^3$ are taken together with the carbon atom to which they are attached to form $C_{4-6}$ saturated hetero ring containing one or two heteroatoms selected independently from nitrogen atom and oxygen atom, said saturated hetero ring may be substituted with 1 to 3 substituents selected independently from the group consisting of fluorine, hydroxy, $C_{1-3}$ alkyl, and $C_{1-3}$ alkoxy.

In a more preferred embodiment of $R^2$ and $R^3$, $R^2$ and $R^3$ are the same or different and are (1) $C_{1-3}$ alkyl which may be substituted with fluorine; or (2) $R^2$ and $R^3$ are taken together with the carbon atom to which they are attached to form $C_{3-6}$ cycloalkyl which may be substituted with fluorine, or (3) $R^2$ and $R^3$ are taken together with the carbon atom to which they are attached to form $C_{4-6}$ saturated hetero ring containing one or two heteroatoms selected independently from nitrogen atom and oxygen atom, said saturated hetero ring may be substituted with fluorine.

The $C_{3-6}$ cycloalkyl which is prepared by taking $R^2$ and $R^3$ together with the carbon atom to which they are attached includes, for example, the following groups.

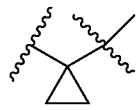
(6a)

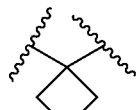
(6b)

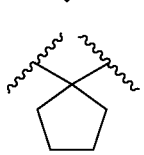
(6c)

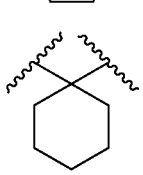
(6d)

The $C_{4-6}$ saturated hetero ring which is prepared by taking $R^2$ and $R^3$ together with the carbon atom to which they are attached includes 4- to 6-membered saturated ring that has one or two heteroatoms selected from the group consisting of nitrogen atom and oxygen atom, which includes, for example, the following groups.

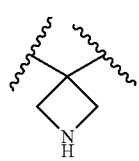
(7a)

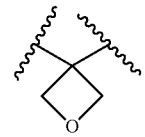
(7b)

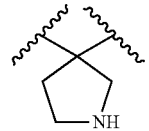
(7c)

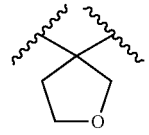
(7d)

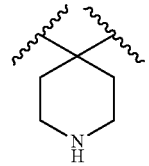
(7e)

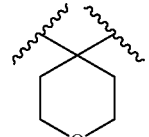
(7f)

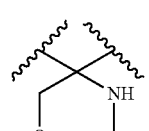
(7g)

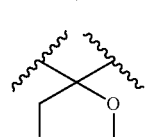
(7h)

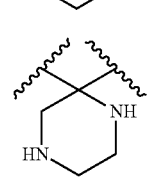
(7i)

In a preferred embodiment of $R^4$ and $R^5$, $R^4$ and $R^5$ are the same or different and are (1) hydrogen,
(2) fluorine,
(3) hydroxy,
(4) $C_{1-3}$ alkyl which may be substituted with 1 to 3 substituents selected independently from the group consisting of fluorine, hydroxy, and $C_{1-3}$ alkoxy,
(5) $C_{3-6}$ cycloalkyl which may be substituted with 1 to 3 substituents selected independently from the group consisting of fluorine, hydroxy, $C_{1-3}$ alkyl, and $C_{1-3}$ alkoxy; or when $R^4$ and $R^5$ are attached to the same carbon atom or to two adjacent carbon atoms respectively,
(6) $R^4$ and $R^5$ may be taken together with the carbon atom(s) to which they are attached to form $C_{3-6}$ cycloalkyl which may be substituted with 1 to 3 substituents selected independently from the group consisting of fluorine, hydroxy, $C_{1-3}$ alkyl, and $C_{1-3}$ alkoxy, or (7) $R^4$ and $R^5$ may be taken together with the carbon atom(s) to which they are attached to form $C_{4-6}$ saturated hetero ring which may be substituted with 1 to 3 substituents selected independently from the group consisting of fluorine, hydroxy, $C_{1-3}$ alkyl, and $C_{1-3}$ alkoxy. The "adjacent carbon atoms" used herein means that two carbon atoms composing the ring are bonded side by side, said carbon atoms are attached to $R^4$ or $R^5$, respectively.

In a more preferred embodiment of $R^4$ and $R^5$, $R^4$ and $R^5$ are the same or different and are (1) hydrogen, (2) fluorine, (3) hydroxy, (4) $C_{1-3}$ alkyl which may be substituted with fluorine, (5) $C_{3-6}$ cycloalkyl which may be substituted with fluorine; or when $R^4$ and $R^5$ are attached to the same carbon atom or to two adjacent carbon atoms respectively, (6) $R^4$ and $R^5$ may be taken together with the carbon atom(s) to which they are attached to form $C_{3-6}$ cycloalkyl which may be substituted with 1 to 3 substituents selected independently from the group consisting of fluorine and $C_{1-3}$ alkyl.

When $R^4$ and $R^5$ are attached to the same carbon atom or to two adjacent carbon atoms respectively, $C_{3-6}$ cycloalkyl which is prepared by taking $R^4$ and $R^5$ together with the carbon atom(s) to which they are attached includes, for example, the following groups.

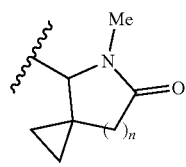
(8a)

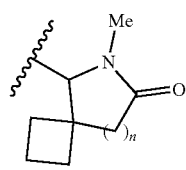
(8b)

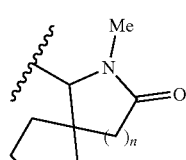
(8c)

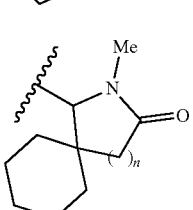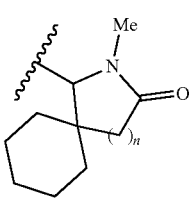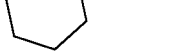
(8d)

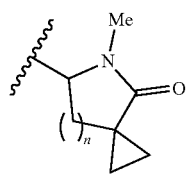
(8e)

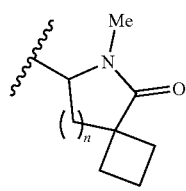
(8f)

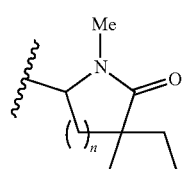
(8g)

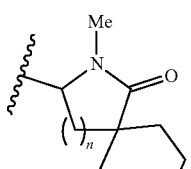
(8h)

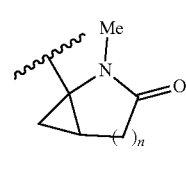
(8i)

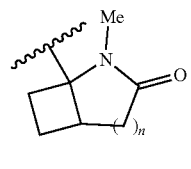
(8j)

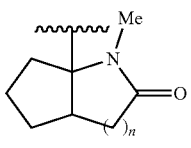
(8k)

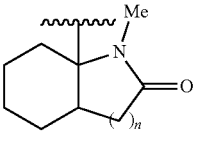
(8l)

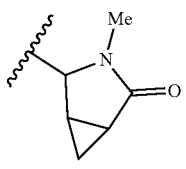
(8m)

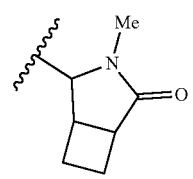 (8n)
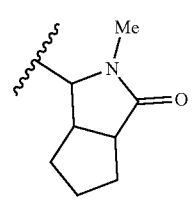 (8o)
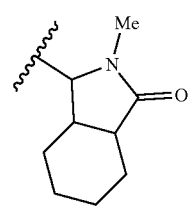 (8p)
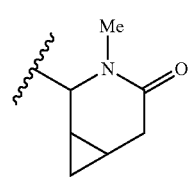 (8q)
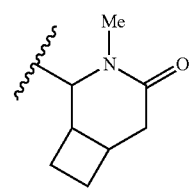 (8r)
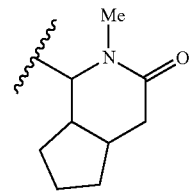 (8s)
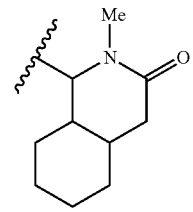 (8t)
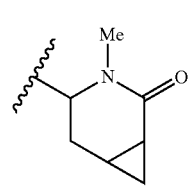 (8u)
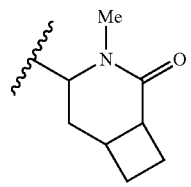 (8v)
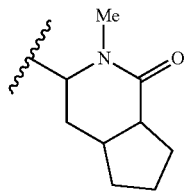 (8w)
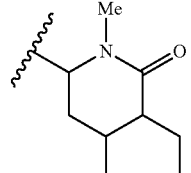 (8x)
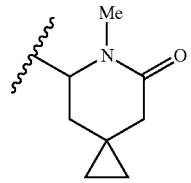 (8y)
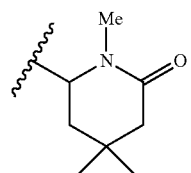 (8z)
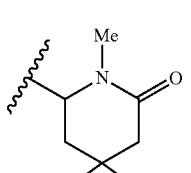 (8aa)
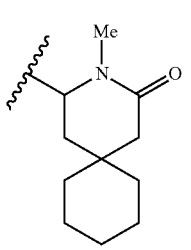 (8ab)
When $R^4$ and $R^5$ are attached to the same carbon atom or to two adjacent carbon atoms respectively, $C_{4-6}$ saturated hetero ring which is prepared by taking $R^4$ and $R^5$ together with the carbon atom(s) to which they are attached includes, for example, the following groups.

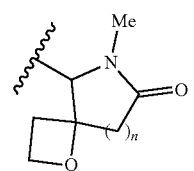
(9a)
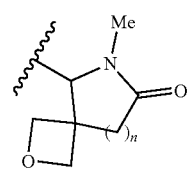
(9b)
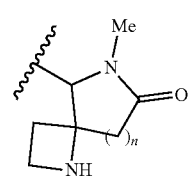
(9c)
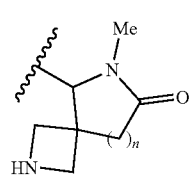
(9d)
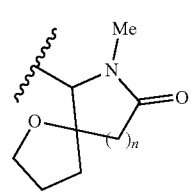
(9e)
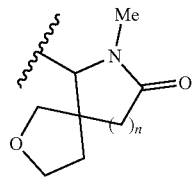
(9f)
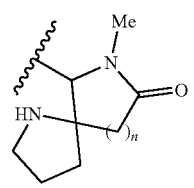
(9g)
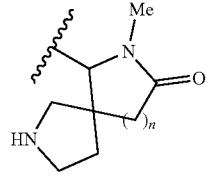
(9h)
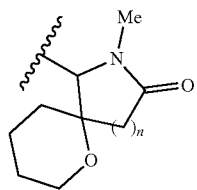
(9i)
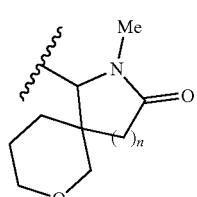
(9j)
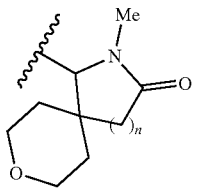
(9k)
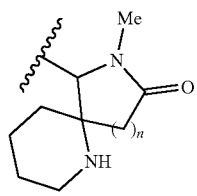
(9l)
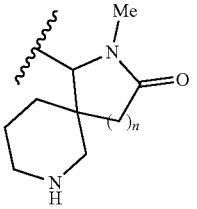
(9m)
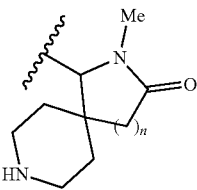
(9n)
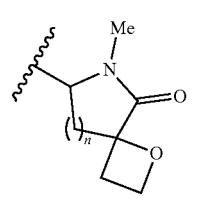
(9o)
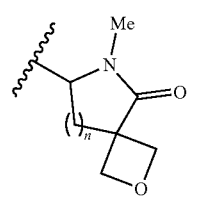
(9p)

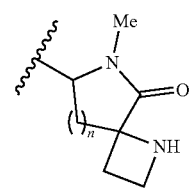 (9q)
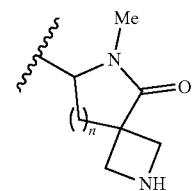 (9r)
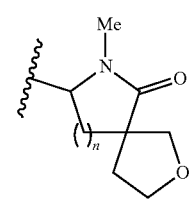 (9s)
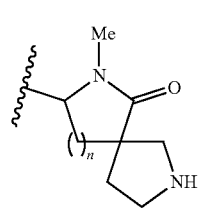 (9t)
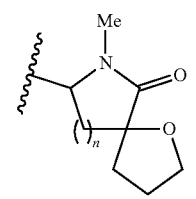 (9u)
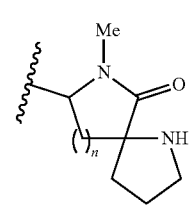 (9v)
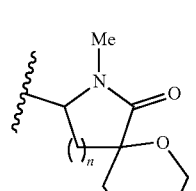 (9w)
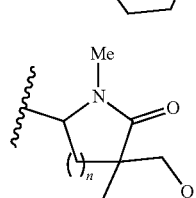 (9x)
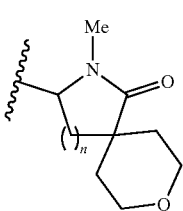 (9y)
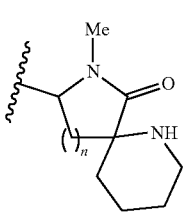 (9z)
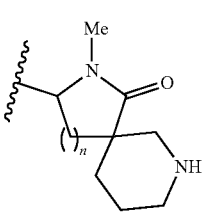 (9aa)
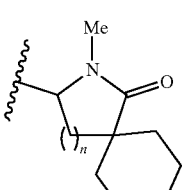 (9ab)
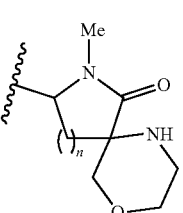 (9ac)
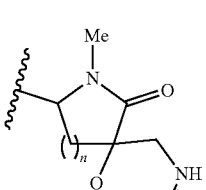 (9ad)
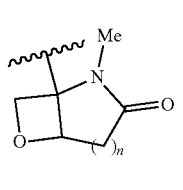 (9ae)
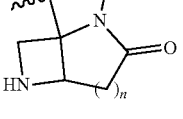 (9af)

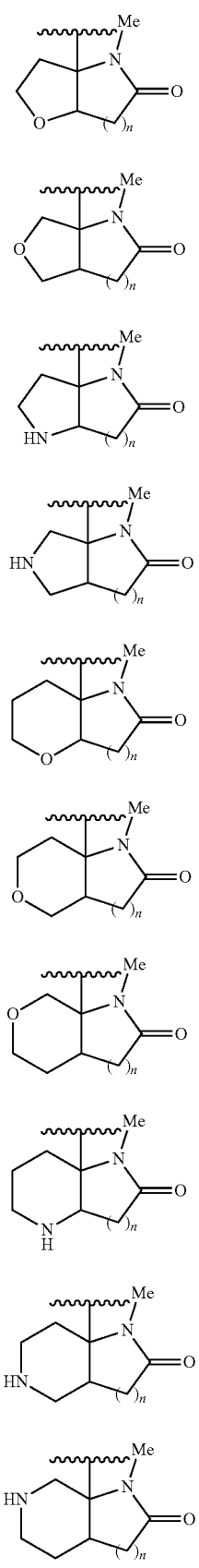
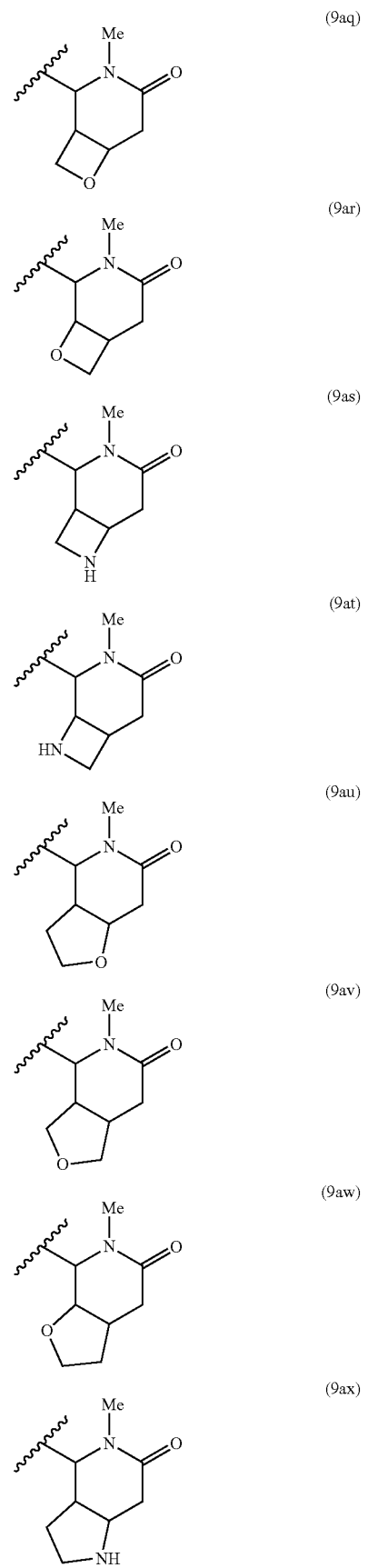

-continued
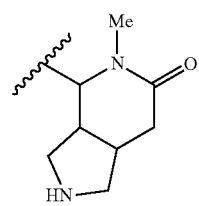
(9ay)
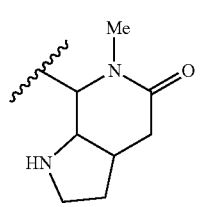
(9az)
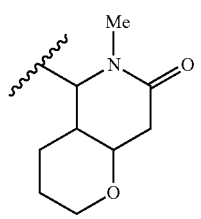
(9ba)
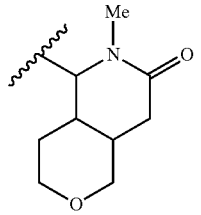
(9bb)
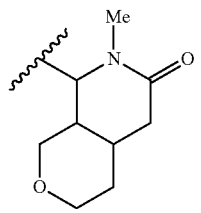
(9bc)
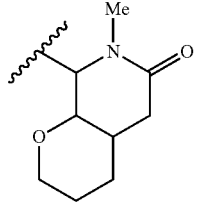
(9bd)
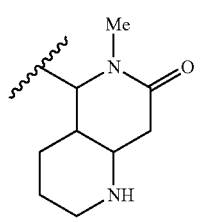
(9be)
-continued
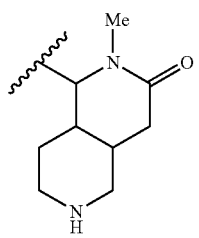
(9bf)
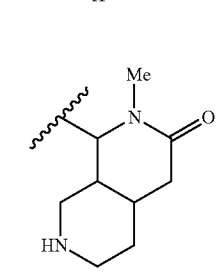
(9bg)
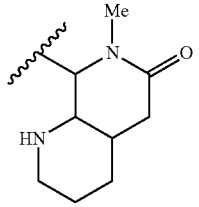
(9bh)
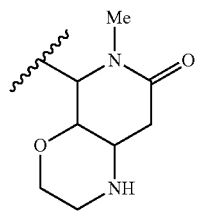
(9bi)
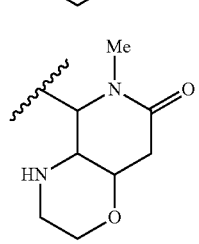
(9bj)
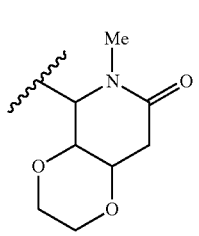
(9bk)
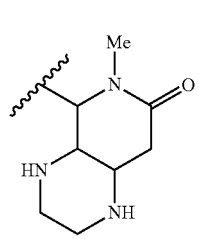
(9bl)

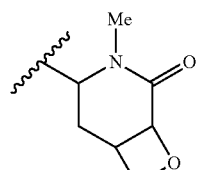 (9bm)
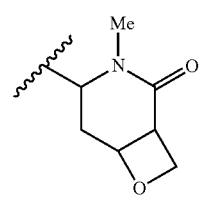 (9bn)
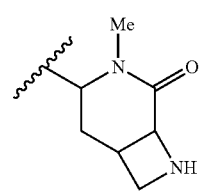 (9bo)
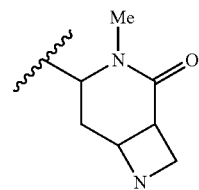 (9bp)
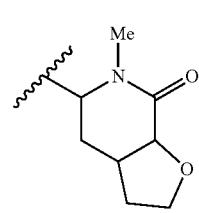 (9bq)
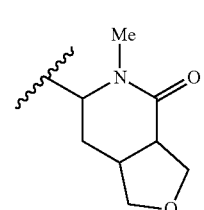 (9br)
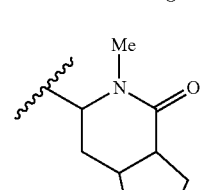 (9bs)
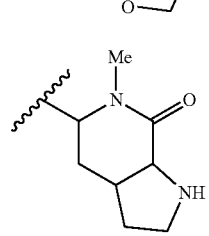 (9bt)
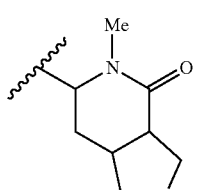 (9bu)
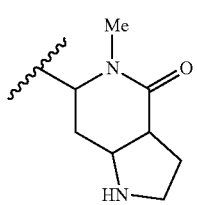 (9bv)
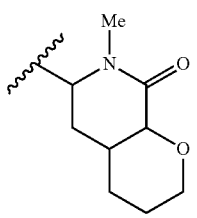 (9bw)
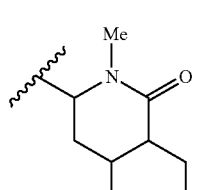 (9bx)
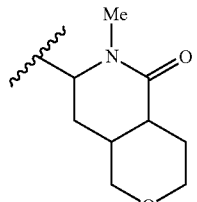 (9by)
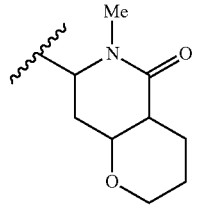 (9bz)
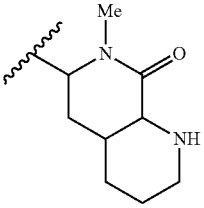 (9ca)

-continued (9cb) 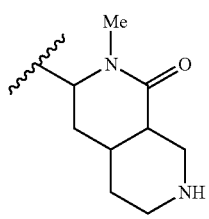

(9cc) 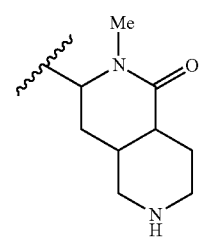

(9cd) 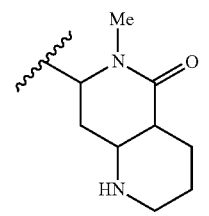

(9ce) 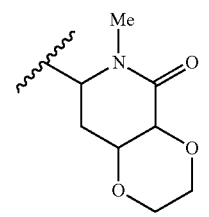

(9cf) 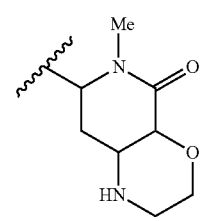

(9cg) 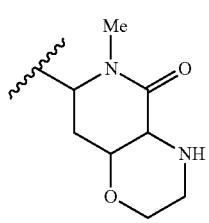

(9ch) 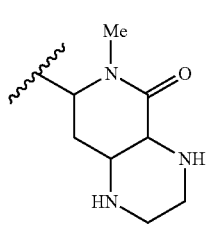

In a preferred embodiment, X, Y, and Z are the same or different and are nitrogen atom or oxygen atom, provided that the ring containing X, Y, and Z includes the following oxadiazoles wherein any two of X, Y, and Z are nitrogen atom and the other is oxygen atom.

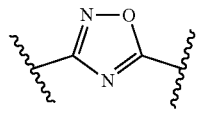 (5a)

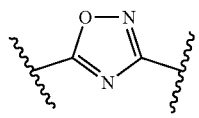 (5b)

(5c)

In above (5a)-(5c), the left binding site is attached to the benzene ring, and the right binding site is attached to $R^1$.

In a preferred embodiment, the ring containing X, Y, and Z includes the following oxadiazoles.

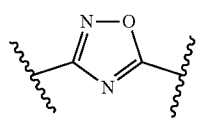 (5a)

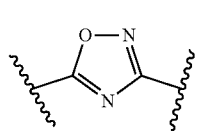 (5b)

In an embodiment, n is an integer of 0, 1, or 2; preferably 0 or 1.

In a preferred embodiment, $Q^1$ is fluorine, chlorine, bromine, or iodine; more preferably fluorine, chlorine, or bromine.

In a preferred embodiment, $Q^2$ is (1) hydrogen,
(2) fluorine,
(3) chlorine,
(4) bromine,
(5) cyano,
(6) $C_{1-3}$ alkyl which may be substituted with fluorine, or
(7) $C_{1-3}$ alkoxy which may be substituted with fluorine.

In a more preferred embodiment, $Q^2$ is (1) hydrogen,
(2) fluorine,
(3) chlorine, or
(4) cyano.

Preferred compounds of formula (1) include the following compounds or a pharmaceutically acceptable salt thereof.

In an embodiment, the present compound of formula (1) includes the following (A).

(A)

A compound of formula (1) or a pharmaceutically acceptable salt thereof, wherein
$R^1$ is any one of the following (2) and (3),

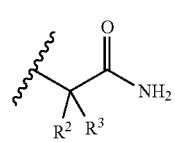

(2)

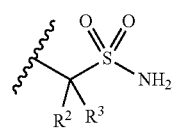

(3)

$R^2$ and $R^3$ are the same or different and are
(1) $C_{1-3}$ alkyl which may be substituted with 1 to 3 substituents selected independently from the group consisting of fluorine, hydroxy, $C_{3-6}$ cycloalkyl, and $C_{1-3}$ alkoxy, or
(2) $C_{3-6}$ cycloalkyl which may be substituted with 1 to 3 substituents selected independently from the group consisting of fluorine, hydroxy, $C_{1-3}$ alkyl, and $C_{1-3}$ alkoxy; or
(3) $R^2$ and $R^3$ are taken together with the carbon atom to which they are attached to form $C_{3-6}$ cycloalkyl which may be substituted with 1 to 3 substituents selected independently from the group consisting of fluorine, hydroxy, $C_{1-3}$ alkyl, and $C_{1-3}$ alkoxy, or
(4) $R^2$ and $R^3$ are taken together with the carbon atom to which they are attached to form $C_{4-6}$ saturated hetero ring containing one or two heteroatoms selected independently from nitrogen atom and oxygen atom, said saturated hetero ring may be substituted with 1 to 3 substituents selected independently from the group consisting of halogen, hydroxy, $C_{1-3}$ alkyl, and $C_{1-3}$ alkoxy,
the ring containing X, Y, and Z is any one of the following (5a) to (5c):

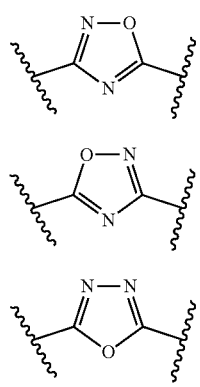

(5a)

(5b)

(5c)

$Q^1$ is fluorine, chlorine, or bromine, and
$Q^2$ is hydrogen, fluorine, chlorine, cyano, $C_{1-3}$ alkyl (which may be substituted with 1 to 3 substituents selected independently from the group consisting of fluorine, $C_{3-6}$ cycloalkyl, and $C_{1-3}$ alkoxy), or $C_{1-3}$ alkoxy (which may be substituted with 1 to 3 substituents selected independently from the group consisting of fluorine, $C_{3-6}$ cycloalkyl, and $C_{1-3}$ alkoxy).

In an embodiment, the present compound of formula (1) includes the following (B).

(B)

A compound of formula (1) or a pharmaceutically acceptable salt thereof, wherein
$R^1$ is the following (4):

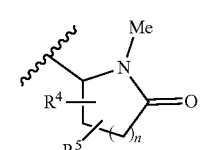

(4)

$R^4$ and $R^5$ are the same or different and are
(1) hydrogen,
(2) halogen,
(3) hydroxy,
(4) $C_{1-3}$ alkyl which may be substituted with 1 to 3 substituents selected independently from the group consisting of halogen, hydroxy, $C_{3-6}$ cycloalkyl, and $C_{1-3}$ alkoxy, or
(5) $C_{3-6}$ cycloalkyl which may be substituted with 1 to 3 substituents selected independently from the group consisting of halogen, hydroxy, $C_{1-3}$ alkyl, and $C_{1-3}$ alkoxy; or
when $R^4$ and $R^5$ are attached to the same carbon atom or to two adjacent carbon atoms respectively,
(6) $R^4$ and $R^5$ may be taken together with the carbon atom(s) to which they are attached to form $C_{3-6}$ cycloalkyl which may be substituted with 1 to 3 substituents selected independently from the group consisting of halogen, hydroxy, $C_{1-3}$ alkyl, and $C_{1-3}$ alkoxy, or
(7) $R^4$ and $R^5$ may be taken together with the carbon atom(s) to which they are attached to form $C_{4-6}$ saturated hetero ring containing one or two heteroatoms selected independently from nitrogen atom and oxygen atom, said saturated hetero ring may be substituted with 1 to 3 substituents selected independently from the group consisting of halogen, hydroxy, $C_{1-3}$ alkyl, and $C_{1-3}$ alkoxy,
the ring containing X, Y, and Z is any one of the following (5a) to (5c):

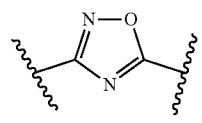

(5a)

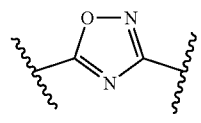

(5b)

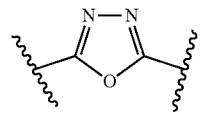

(5c)

$Q^1$ is fluorine, chlorine, or bromine,
$Q^2$ is hydrogen, fluorine, chlorine, cyano, $C_{1-3}$ alkyl (which may be substituted with 1 to 3 substituents selected independently from the group consisting of fluorine, $C_{3-6}$ cycloalkyl, and $C_{1-3}$ alkoxy), or $C_{1-3}$ alkoxy (which may be substituted with 1 to 3 substituents selected independently from the group consisting of fluorine, $C_{3-6}$ cycloalkyl, and $C_{1-3}$ alkoxy), and
n is preferably an integer of 0, 1, or 2.

In an embodiment, the present compound of formula (1) includes the following (C).

(C)

A compound of formula (1) or a pharmaceutically acceptable salt thereof, wherein $R^1$ is any one of the following (2) and (3),

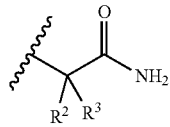

(2)

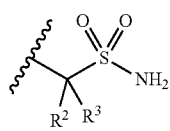

(3)

$R^2$ and $R^3$ are the same or different and are (1) $C_{1-3}$ alkyl which may be substituted with fluorine; or (2) $R^2$ and $R^3$ are taken together with the carbon atom to which they are attached to form $C_{3-6}$ cycloalkyl which may be substituted with fluorine, or (3) $R^2$ and $R^3$ are taken together with the carbon atom to which they are attached to form $C_{4-6}$ saturated hetero ring containing one or two heteroatoms selected independently from nitrogen atom and oxygen atom, said saturated hetero ring may be substituted with fluorine, the hereto aryl ring containing X, Y, and Z is the following (5a) or (5b):

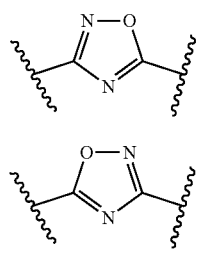

(5a)

(5b)

$Q^1$ is fluorine, chlorine, or bromine, and $Q^2$ is hydrogen, fluorine, chlorine, or cyano.

In an embodiment, the present compound of formula (1) includes the following (D).

(D)

A compound of formula (1) or a pharmaceutically acceptable salt thereof, wherein $R^1$ is the following (4),

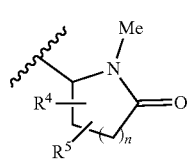

(4)

$R^4$ and $R^5$ are the same or different and are (1) hydrogen, (2) fluorine, (3) hydroxy, (4) $C_{1-3}$ alkyl which may be substituted with fluorine, or (5) $C_{3-6}$ cycloalkyl which may be substituted with fluorine; or when $R^4$ and $R^5$ are attached to the same carbon atom or to two adjacent carbon atoms respectively, (6) $R^4$ and $R^5$ may be taken together with the carbon atom(s) to which they are attached to form $C_{3-6}$ cycloalkyl which may be substituted with 1 to 3 substituents selected independently from the group consisting of fluorine and $C_{1-3}$ alkyl, the hereto aryl ring containing X, Y, and Z is the following (5a) or (5b),

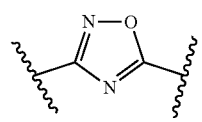

(5a)

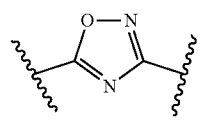

(5b)

$Q^1$ is fluorine, chlorine, or bromine, and $Q^2$ is hydrogen, fluorine, chlorine, or cyano.

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; or organic acid salts such as citrate, oxalate, phthalate, fumarate, maleate, succinate, malate, acetate, formate, propionate, benzoate, trifluoroacetate, methanesulfonate, benzenesulfonate, para-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. The "pharmaceutically acceptable salt" also includes amino acid salts of basic or acidic amino acids such as arginine, lysine, ornithine, aspartate, and glutamate.

The suitable salts of starting materials and intermediates and the acceptable salts of drug substances are conventional non-toxic salts. The suitable salt includes, for example, acid addition salts such as organic acid salts (including acetate, trifluoroacetate, maleate, fumarate, citrate, tartrate, methanesulfonate, benzenesulfonate, formate, and para-toluenesulfonate) and inorganic acid salts (including hydrochloride, hydrobromide, hydroiodide, sulfate, nitrate, and phosphate); salts with amino acids (including arginine, aspartate, and glutamate); metal salts such as alkali metal salts (including sodium salts and potassium salts) and alkaline earth metal salts (including calcium salts and magnesium salts); ammonium salts; organic base salts (including trimethylamine salts, triethylamine salts, pyridine salts, picolinate, dicyclohexylamine salts, and N,N'-dibenzylethylenediamine salts); and other salts which a person skilled in the art can optionally select.

If the compound of the present invention needs to be obtained as a salt thereof, when the compound of the present invention is obtained as a salt, it may be purified as it is, and when it is obtained in a free form, it may be solved or suspended in an appropriate organic solvent and an acid or base may be added therein to form a salt by a common method.

The compound of formula (1) in which any one or more $^1$H atoms are replaced by 2H(D) atoms is also within the scope of the present invention of formula (1).

The present invention encompasses compounds of formula (1) or pharmaceutically acceptable salts thereof. As the compound of the present invention may exist in a form of hydrate and/or solvate of various solvents, including solvate (ethanolate and like), and these hydrate and/or solvate are included in the compound of the present invention. In addition, the present invention encompasses all tautomers of the compound (1), all possible stereoisomers thereof, crystalline forms thereof in various states, and mixtures thereof.

The compound of formula (1) encompasses optical isomers based on an optically active center, atropisomers based on axial or planar chirality caused by restriction of intramolecular rotation, and all other isomers which can exist as stereoisomers, tautomers, and geometric isomers, and mixtures thereof.

Especially, each optical isomer and atropisomer can be obtained as a racemate, or as an optically active substance when an optically active starting material or intermediate is used. Racemates of corresponding starting materials, intermediates, or final products can also be physically or chemically resolved into optical enantiomers by a known isolating method such as a method with an optically active column and a fractional crystallization method, at an appropriate step in the above preparation processes, if necessary. These methods for resolving enantiomers include a diastereomer method in which, for example, a racemate is reacted with an optically active resolving agent to synthesize two kinds of diastereomers, which are resolved by fractional crystallization or a similar method through different physical properties.

Processes to prepare the compounds of the present invention are mentioned below, but the processes to prepare the compound of the present invention should not be limited thereto.

Preparation Process 1

In the compound of formula (I), the compound of the following formula (Ia) can be prepared by the following preparation process.

Wherein $R^2$, $R^3$, $Q^1$, $Q^2$, X, Y, and Z are as defined in Item 1.

Compound (Ia) can be prepared by amidating Compound (IIa) with ammonia. The amidation of Compound (IIa) can be carried out in a conventional manner. For example, the reaction can be performed by converting Compound (IIa) to a reactive derivative (such as lower alkyl ester, active ester, acid anhydride, and acid halide), and reacting the prepared reactive derivative with ammonia. The active ester includes, for example, p-nitrophenyl ester, N-hydroxysuccinimide ester, and pentafluorophenyl ester. The acid anhydride includes, for example, a mixed anhydride of Compound (IIa) which is prepared with ethyl chlorocarbonate, isobutyl chlorocarbonate, isovaleric acid, pivalic acid, etc. The solvent used herein should be selected based on a starting compound used herein and other factors, which includes, for example, THF, dioxane, DME, acetonitrile, DMF, toluene, ethyl acetate, and isopropyl acetate. The solvent may be used as a single or a combination thereof. The reaction temperature should not be limited to a particular temperature, but which is selected from the range of generally −20° C. to boiling point of a solvent used herein, and preferably 0° C. to 30° C. The reaction time is generally 30 minutes to 24 hours.

In addition, Compound (Ia) can be also prepared by reacting Compound (IIa) with an ammonium salt such as $(NH_4)_2CO_3$ in the presence of a condensation agent. The condensation agent used herein includes, for example, N,N'-dicyclohexylcarbodiimide, 1-ethyl-3-(3-dimethylaminopropyl)carbodiimide monohydrochloride, N,N'-carbonyldiimidazole, and benzotriazol-1-yl-oxytris(pyrrolidino)phosphonium-hexafluorophosphate. These condensation agents may be used each alone or in combination with a reagent for peptide synthesis such as N-hydroxysuccinimide and N-hydroxybenzotriazole. The solvent used herein should be selected based on a starting compound used herein and other factors, which includes, for example, THF, dioxane, DME, acetonitrile, DMF, toluene, ethyl acetate, and isopropyl acetate. The solvent may be used as a single or a mixture of solvents thereof. The reaction temperature should not be limited to a particular temperature, but which is selected from the range of generally −20° C. to boiling point of a solvent used herein, and preferably 0° C. to 30° C. The reaction time is generally 30 minutes to 24 hours.

Preparation Process 2

In the compound of formula (I), the compound of the following formula (Ib) can be prepared by the following preparation process.

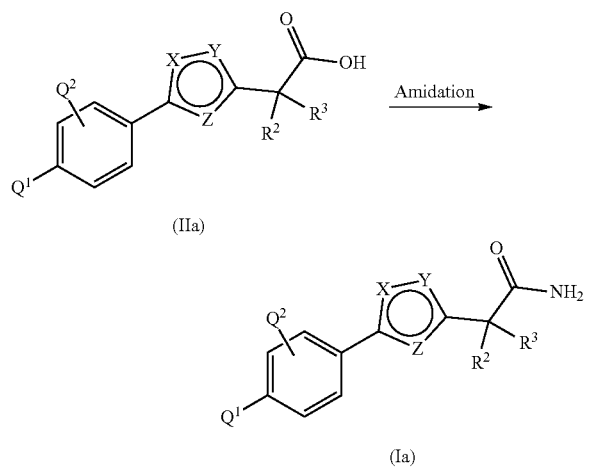

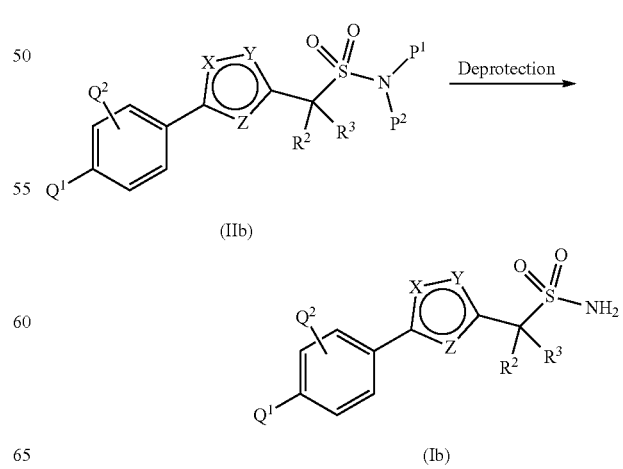

Wherein $R^1$, $R^3$, $Q^1$, $Q^2$, X, Y, and Z are as defined in Item 1; $P^1$ is a protecting group for a nitrogen atom such as 2,4-dimethoxybenzyl group and p-methoxybenzyl group, which can be removed under an acidic condition; and $P^2$ is hydrogen or a protecting group for a nitrogen atom such as 2,4-dimethoxybenzyl group and p-methoxybenzyl group, which can be removed under an acidic condition.

Compound (Ib) can be prepared by deprotecting Compound (IIb). The deprotection of Compound (IIb) can be performed in a conventional manner. For example, the deprotection reaction can be performed by reacting Compound (IIb) with an organic strong acid such as trifluoroacetic acid, methanesulfonic acid, and trifluoromethanesulfonic acid; or an inorganic strong acid such as hydrochloric acid, sulfuric acid, and nitric acid.

The deprotection of Compound (IIb) can be performed in a solvent or in the absence of solvents. The solvent used herein should be selected based on a starting compound used herein and other factors, which includes, for example, toluene, THF, dioxane, DME, dichloromethane, chloroform, ethyl acetate, isopropyl acetate, acetone, acetonitrile, DMF, and DMSO. The solvent may be used as a single or a mixture of solvents thereof. As a protecting group for the nitrogen atom in Compound (IIb), t-butoxycarbonyl group, t-butyl group, p-methoxybenzyl group, and the like may be also used besides 2,4-dimethoxybenzyl group, which can be removed under acidic conditions. Depending on the type of protecting group, only one protecting group may be selected from protection of the nitrogen atom. The reaction temperature may vary depending on a starting compound used herein and other factors, which is generally about −30° C. to about 150° C., and preferably about −10° C. to about 70° C. The reaction time is generally 30 minutes to 24 hours.

Preparation Process 3

In the compound of formula (I), the compound of the following formula (1c) can be prepared by the following preparation process.

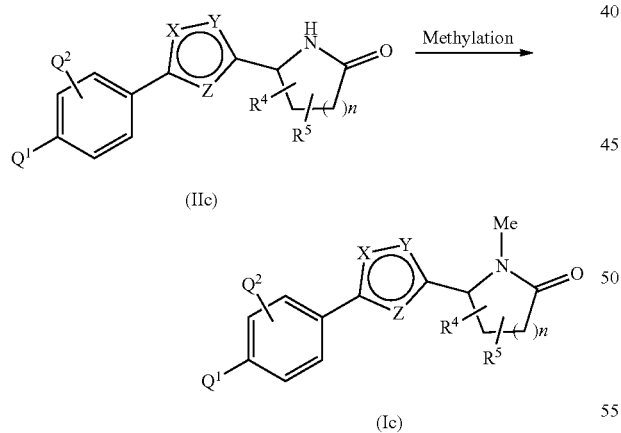

(IIc)

(Ic)

Wherein $R^4$, $R^5$, $Q^1$, $Q^2$, X, Y, Z, and n are as defined in Item 1.

Compound (Ic) can be prepared by methylating Compound (IIc). The methylation of Compound (IIc) can be performed in a conventional manner. For example, the methylation reaction can be performed by reacting Compound (IIc) with methylating agent such as methyl iodide, methyl bromide, and dimethyl sulfate in the presence of a base in an appropriate solvent. The solvent used herein should be selected based on a starting compound used herein and other factors, which includes, for example, toluene, THF, dioxane, DME, ethyl acetate, isopropyl acetate, acetone, acetonitrile, DMF, and NMP. The solvent may be used as a single or a mixture of solvents thereof. The base used herein includes, for example, alkali metal hydroxides such as sodium hydroxide, potassium hydroxide, and lithium hydroxide; alkali metal hydrides such as sodium hydride and potassium hydride; alkali metal alkoxides such as potassium t-butoxide and sodium methoxide; and alkali metal carbonates such as sodium carbonate, sodium bicarbonate, potassium carbonate, and cesium carbonate. The reaction temperature may vary depending on a starting compound used herein and other factors, which is generally about −30° C. to about 150° C., and preferably about −10° C. to about 70° C. The reaction time is generally 30 minutes to 24 hours.

The compounds of formulae (Ia), (Ib), and (Ic) which are prepared in the above Preparation processes 1, 2, and 3 can be isolated and purified in a conventional manner such as chromatography and recrystallization.

The starting compounds used in the above Preparation processes 1, 2, and 3 can be prepared in the processes mentioned below.

Preparation Process 4

In the compound of formula (I), the compound of the following formula (1c') can be also prepared by the following preparation process.

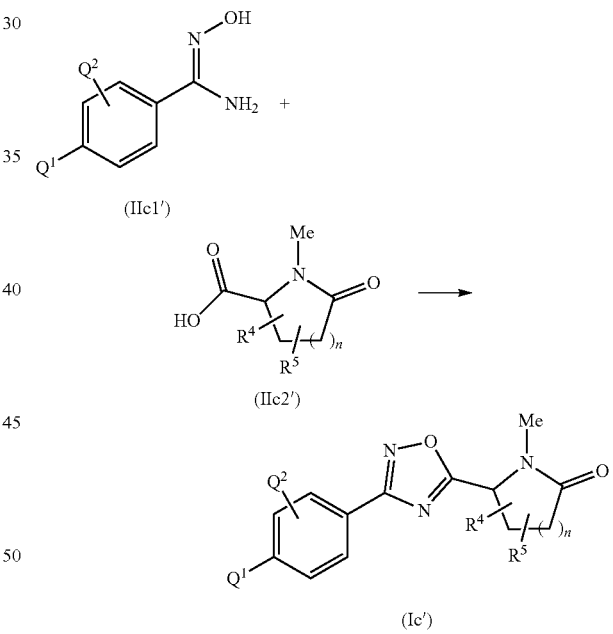

Wherein $R^4$, $R^5$, $Q^1$, $Q^2$, and n are as defined in Item 1.

Compound (Ic') can be prepared by reacting Compound (IIc1') and Compound (IIc2') in the presence of a condensation agent. The condensation agent used herein includes, for example, N,N'-dicyclohexylcarbodiimide, 1-ethyl-3-(3-dimethylaminopropyl)carbodiimide monohydrochloride, N,N'-carbonyldiimidazole, benzotriazol-1-yl-oxytris(pyrrolidino)phosphonium-hexafluorophosphate, 1-[bis(dimethylamino)methylene]-1H-1,2,3-triazolo[4,5-b]pyridinium 3-oxide hexafluorophosphate, 2-chloro-1,3-dimethylimidazolinium-hexafluorophosphate, 1-(chloro-1-pyrrolidinylmethylene)pyrrolidinium-hexafluorophosphate, bromotris(pyrrolidino)phosphonium-hexafluorophosphate, and propylphosphonic acid anhydride. These condensation agents may be used each alone or in combination with a reagent for peptide synthesis such as N-hydroxysuccinimide and N-hydroxybenzotriazole. The solvent used herein should be selected based on a starting compound used herein and other factors, which includes, for example, THF, dioxane, DME, acetonitrile, DMF, toluene, pyridine, ethyl acetate, and isopropyl acetate. The solvent may be used as a single or a mixture of solvents thereof. The reaction temperature may vary depending on a starting compound used herein and other factors, which is generally −100° C. to 200° C., and preferably −30° C. to 150° C. The reaction time is generally 30 minutes to 24 hours.

Preparation Process 5

Compound (IIa) which is used in the above Preparation process 1 can be prepared according to the process in the following scheme.

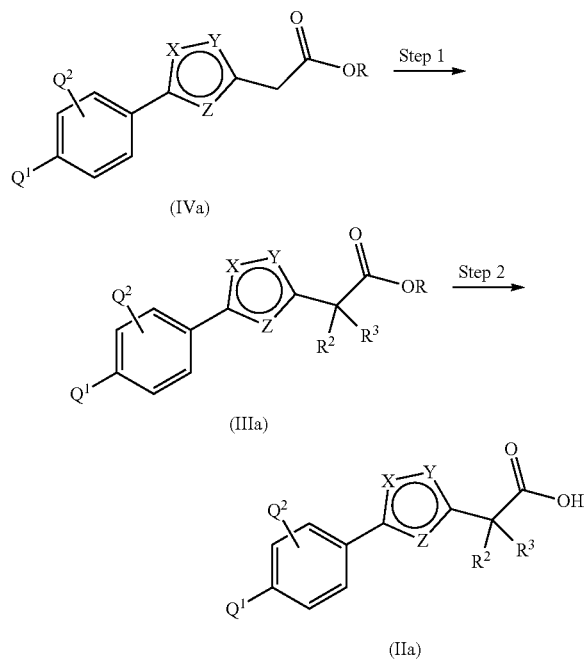

Wherein $R^2$, $R^3$, $Q^1$, $Q^2$, X, Y, and Z are as defined in Item 1, and R is $C_{1-6}$ alkyl.

(Step 1)

Compound (IIIa) can be prepared by alkylating Compound (IVa). The alkylation of Step 1 can be performed in a conventional manner. For example, the reaction can be performed by reacting Compound (IVa) with alkyl halide or cycloalkyl halide which is denoted by $R^2X$ or $R^3X$ in the presence of a base in an appropriate solvent. Compound (IIIa) wherein $R^2$ and $R^3$ are taken together with the carbon atom to which they are attached to form $C_{3-6}$ cycloalkyl or 4- to 6-membered saturated hetero ring can be prepared by reacting Compound (IVa) with the corresponding dihalogenated compound (for example, X—$(CH_2)_n$—X wherein n is an integer of 3 to 6, and X is halogen) under the above reaction condition. The solvent used herein should be selected based on a starting compound used herein and other factors, which includes, for example, THF, dioxane, DME, acetonitrile, DMF, toluene, ethyl acetate, and isopropyl acetate. The solvent may be used as a single or a mixture of solvents thereof. The base used herein includes, for example, alkali metal hydroxides such as sodium hydroxide, potassium hydroxide, and lithium hydroxide; alkali metal hydrides such as sodium hydride and potassium hydride; alkali metal alkoxides such as potassium t-butoxide and sodium methoxide; and alkali metal carbonates such as sodium carbonate, sodium bicarbonate, potassium carbonate, and cesium carbonate. The reaction temperature may vary depending on a starting compound used herein and other factors, which is generally 0° C. to 200° C., and preferably 20° C. to 150° C. The reaction time is generally 30 minutes to 24 hours.

(Step 2)

Compound (IIa) can be prepared by hydrolyzing Compound (IIIa). The hydrolysis of Step 2 can be performed in a conventional manner. For example, the reaction can be performed by treating Compound (IIIa) with water under an acidic or basic condition in an appropriate solvent. The solvent used herein should be selected based on a starting compound used herein and other factors, which includes, for example, THF, dioxane, DME, acetone, acetonitrile, DMF, DMSO, methanol, ethanol, isopropanol, and water. The solvent may be used as a single or a mixture of solvents thereof. The acid used herein includes, for example, a mineral acid such as hydrochloric acid and sulfuric acid. The base used herein includes, for example, alkali metal hydroxides such as sodium hydroxide, potassium hydroxide, and lithium hydroxide; alkali metal alkoxides such as potassium t-butoxide; and alkali metal carbonates such as sodium carbonate, potassium carbonate, and lithium carbonate. The reaction temperature may vary depending on a starting compound used herein and other factors, which is generally 0° C. to 150° C., and preferably 20° C. to 100° C. The reaction time is generally 30 minutes to 24 hours.

Preparation Process 6

In Compound (IIIa) which is used in the above Preparation process 5, the compound of the following formula (IIIa') can be prepared by condensation reaction accompanied with dehydration and cyclization reaction of Compound (IIIa1) and Compound (IIIa2).

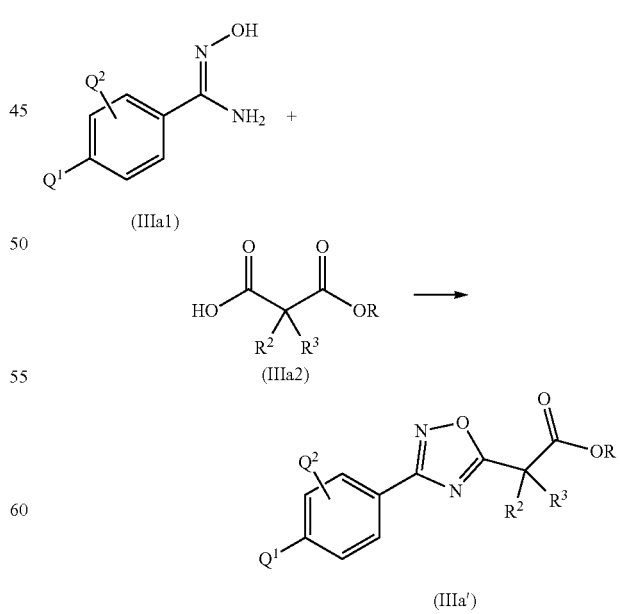

Wherein $R^2$, $R^3$, $Q^1$, and $Q^2$ are as defined in Item 1, and R is $C_{1-6}$ alkyl.

The condensation reaction accompanied with dehydration and cyclization reaction of Compound (IIIa1) and Compound (IIIa2) can be performed in a conventional manner. For example, the reaction can be performed by converting Compound (IIIa2) to a reactive derivative (such as lower alkyl ester, active ester, acid anhydride, and acid halide) and then reacting the prepared reactive derivative with Compound (IIIa1). The active ester includes, for example, p-nitrophenyl ester, N-hydroxysuccinimide ester, and pentafluorophenyl ester. The acid anhydride includes, for example, a mixed anhydride prepared from ethyl chlorocarbonate, isobutyl chlorocarbonate, isovaleric acid, pivalic acid, etc. The solvent used herein should be selected based on a starting compound used herein and other factors, which includes, for example, THF, dioxane, DME, acetonitrile, DMF, toluene, pyridine, and esters such as ethyl acetate, isopropyl acetate. The solvent may be used as a single or a mixture of solvents thereof. The reaction temperature may vary depending on a starting compound used herein and other factors, which is generally −100° C. to 200° C., and preferably −30° C. to 150° C. The reaction time is generally 30 minutes to 24 hours.

In addition, Compound (IIIa') can be also prepared by reacting Compound (IIIa1) and Compound (IIIa2) in the presence of a condensation agent. The condensation agent used herein includes, for example, N,N'-dicyclohexylcarbodiimide, 1-ethyl-3-(3-dimethylaminopropyl)carbodiimide monohydrochloride, N,N'-carbonyldiimidazole, and benzotriazol-1-yl-oxytris(pyrrolidino)phosphonium-hexafluorophosphate. These condensation agents may be used each alone or in combination with a reagent for peptide synthesis such as N-hydroxysuccinimide and N-hydroxybenzotriazole. The solvent used herein should be selected based on a starting compound used herein and other factors, which includes, for example, THF, dioxane, DME, acetonitrile, DMF, toluene, pyridine, ethyl acetate, and isopropyl acetate. The solvent may be used as a single or a mixture of solvents thereof. The reaction temperature may vary depending on a starting compound used herein and other factors, which is generally −100° C. to 200° C., and preferably −30° C. to 150° C. The reaction time is generally 30 minutes to 24 hours.

Preparation Process 7

In Compound (IVa) which is used in the above Preparation process 5, the compound of the following formula (IVa') can be prepared by condensation reaction accompanied with dehydration and cyclization reaction of Compound (IVa1) and Compound (IVa2).

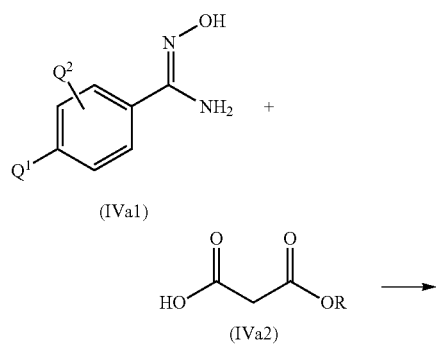

(IVa1)

(IVa2)

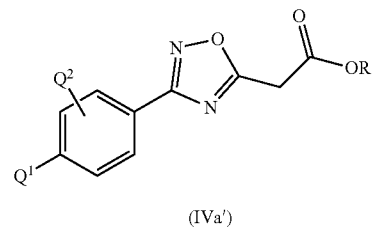

(IVa')

Wherein $Q^1$ and $Q^2$ are as defined in Item 1, and R is $C_{1-6}$ alkyl.

Compound (IVa') can be prepared from Compound (IVa1) and Compound (IVa2) by the process of Preparation process 6.

Preparation Process 8

In Compound (IVa) which is used in the above Preparation process 5, the compound of the following formula (IVa") can be prepared by condensation reaction accompanied with dehydration and cyclization reaction of Compound (IVa3) and Compound (IVa4).

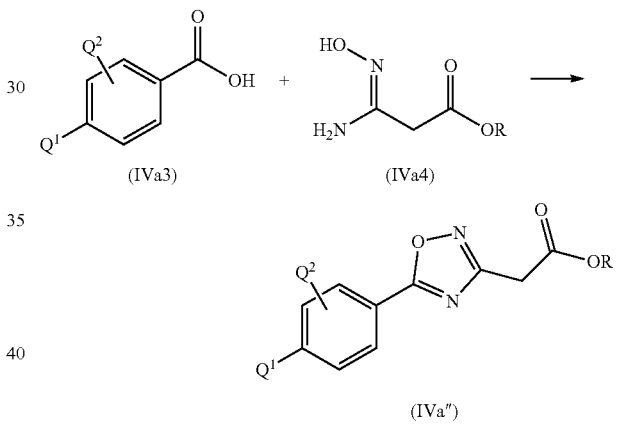

(IVa3)                (IVa4)

(IVa")

Wherein $Q^1$ and $Q^2$ are as defined in Item 1, and R is $C_{1-6}$ alkyl.

Compound (IVa") can be prepared from Compound (IVa3) and Compound (IVa4) by the process of Preparation process 6.

Preparation Process 9

In Compound (IVa) which is used in the above Preparation process 5, the compound of the following formula (IVa''') can be prepared by condensation reaction accompanied with dehydration and cyclization reaction of Compound (IVa5) and Compound (IVa6).

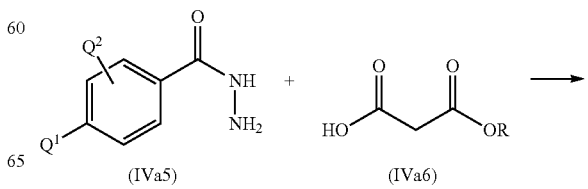

(IVa5)                (IVa6)

-continued

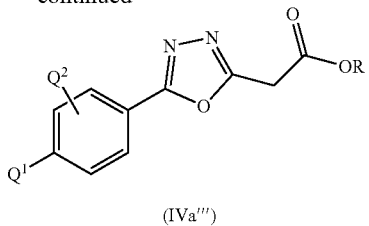

(IVa''')

Wherein $Q^1$ and $Q^2$ are as defined in Item 1, and R is $C_{1-6}$ alkyl.

Compound (IVa''') can be prepared from Compound (IVa5) and Compound (IVa6) according to the process of Preparation process 6. The production of a 1,3,4-oxadiazole ring treated with dehydration and cyclization reaction may be performed in coexistence with a dehydrating agent such as phosphorus oxychloride and Burgess reagent as an additive.

Preparation Process 10

Compound (IIb) which is used in the above Preparation process 2 can be prepared by the process in the following scheme.

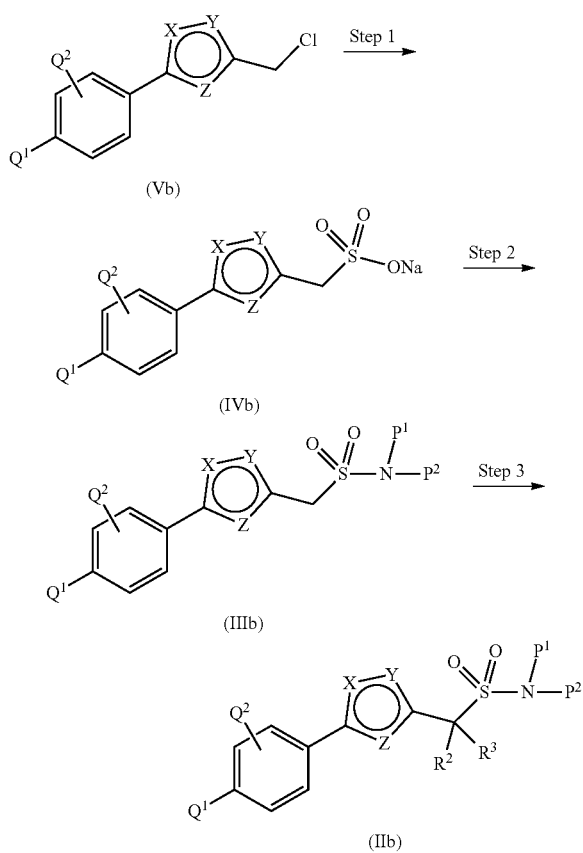

Wherein $R^2$, $R^3$, $Q^1$, $Q^2$, X, Y, and Z are as defined in Item 1; $P^1$ is a protecting group for a nitrogen atom such as 2,4-dimethoxybenzyl group and p-methoxybenzyl group, which can be removed under an acidic condition; and $P^2$ is hydrogen or a protecting group for a nitrogen atom such as 2,4-dimethoxybenzyl group and p-methoxybenzyl group, which can be removed under an acidic condition.

(Step 1)

Compound (IVb) can be prepared by reacting Compound (Vb) with sodium sulfite. The substitution reaction of Step 1 can be performed in a conventional manner. For example, the reaction can be performed by treating Compound (Vb) with sodium sulfite in a suitable solvent. The solvent used herein should be selected based on a starting compound used herein and other factors, which includes, for example, ethers such as Et$_2$O, THF, dioxane, and DME; alcohols such as methanol, ethanol, and isopropyl alcohol; and toluene. The solvent may be used as a single or a mixture of solvents thereof. The reaction temperature may vary depending on a starting compound used herein and other factors, which is generally −100° C. to 200° C., and preferably 0° C. to 150° C. The reaction time is generally 30 minutes to 24 hours.

(Step 2)

Compound (IIIb) can be prepared by sulfonamidating Compound (IVb). The sulfonamidation of Step 2 can be performed in a conventional manner. For example, the reaction can be performed by transforming Compound (IVb) into the sulfonyl chloride compound and then reacting the obtained compound with an amine compound. The transforming to sulfonyl chloride compound may be performed with phosphorus oxychloride in a solvent or in the absence of solvents. The solvent used herein should be selected based on a starting compound used herein and other factors, which includes, for example, Et$_2$O, THF, dioxane, DME, and toluene. The solvent may be used as a single or a mixture of solvents thereof. The reaction temperature may vary depending on a starting compound used herein and other factors, which is generally −100° C. to 200° C., and preferably 0° C. to 150° C. The reaction time is generally 30 minutes to 24 hours.

The transforming from sulfonyl chloride compound which is an intermediate in Step 2 to the corresponding sulfonamide compound may be performed in the presence or absence of a base in a solvent with NHP$^1$P$^2$ which is an amine compound mono- or di-substituted with protecting group which can be removed under an acidic condition. The solvent used herein should be selected based on a starting compound used herein and other factors, which includes, for example, Et$_2$O, THF, dioxane, DME, DMF, acetonitrile, and toluene. The solvent may be used as a single or a mixture of solvents thereof. The base used herein includes, for example, alkali metal hydroxides such as sodium hydroxide, potassium hydroxide, and lithium hydroxide; alkali metal alkoxides such as potassium t-butoxide; alkali metal carbonates such as sodium carbonate, potassium carbonate, and lithium carbonate; and organic bases such as triethylamine, N,N-diisopropylethylamine, pyridine, 2,6-lutidine, 2,4,6-collidine, and 4-dimethylaminopyridine. The reaction temperature may vary depending on a starting compound used herein and other factors, which is generally −100° C. to 200° C., and preferably 0° C. to 150° C. The reaction time is generally 30 minutes to 24 hours.

(Step 3)

Compound (IIb) can be prepared by alkylating Compound (IIIb). Compound (IIb) can be prepared from Compound (IIIb) by the process of Preparation process 5, Step 1.

Preparation Process 11

In Compound (Vb) which is used in the above Preparation process 10, the compound of the following formula (Vb') can be prepared by condensation-cyclodehydration reaction of Compound (Vb1) and Compound (Vb2).

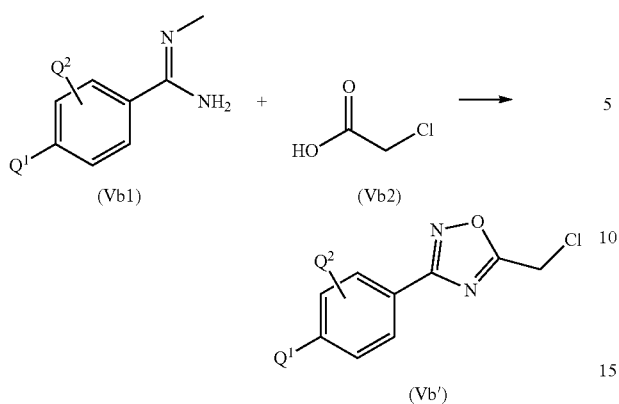

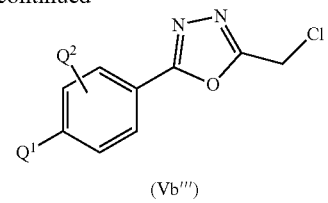

Wherein $Q^1$ and $Q^2$ are as defined in Item 1.

Compound (Vb') can be prepared from Compound (Vb1) and Compound (Vb2) by the process of Preparation process 6.

Preparation Process 12

In Compound (Vb) which is used in the above Preparation process 10, the compound of the following formula (Vb") can be prepared by condensation reaction accompanied with dehydration and cyclization reaction of Compound (Vb3) and Compound (Vb4).

Wherein $Q^1$ and $Q^2$ are as defined in Item 1.

Compound (Vb''') can be prepared from Compound (Vb5) and Compound (Vb6) by the process of Preparation process 9.

Preparation Process 14

In Compound (IIc) which is used in the above Preparation process 3, the compound of the following formula (IIc') can be prepared by condensation reaction accompanied with dehydration and cyclization reaction of Compound (IIc1) and Compound (IIc2).

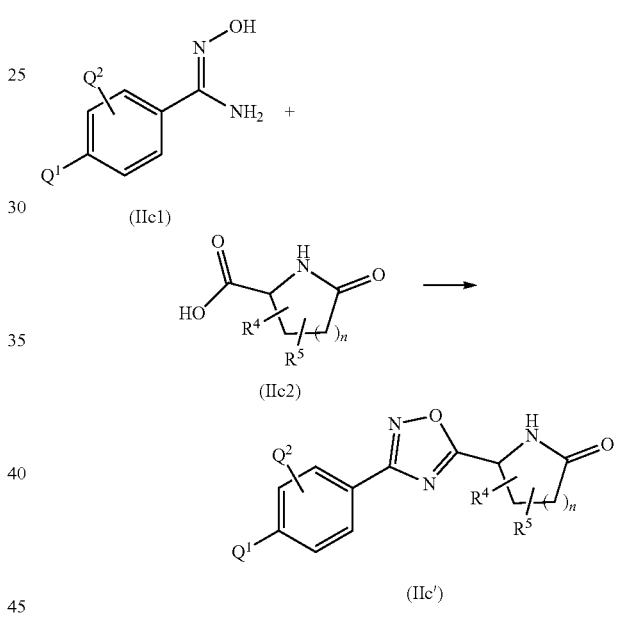

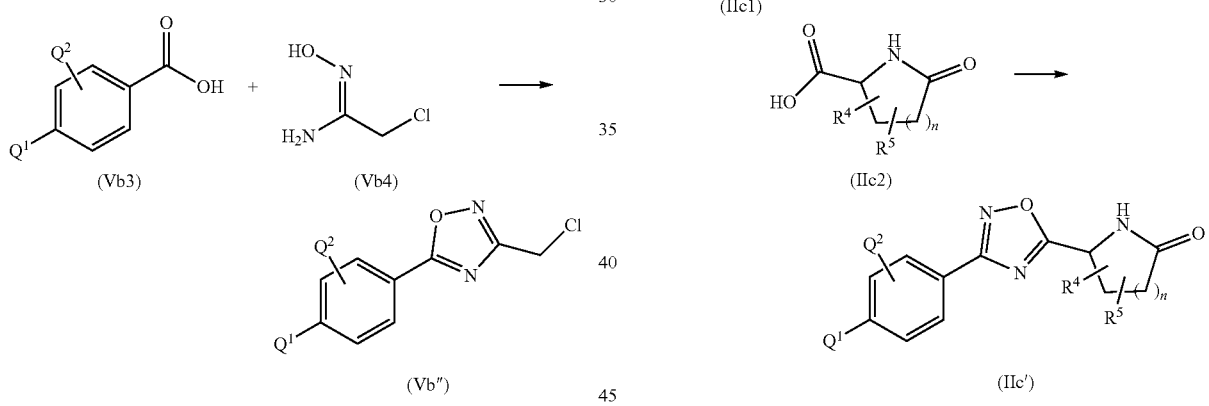

Wherein $Q^1$ and $Q^2$ are as defined in Item 1.

Compound (Vb") can be prepared from Compound (Vb3) and Compound (Vb4) by the process of Preparation process 6.

Preparation Process 13

In Compound (Vb) which is used in the above Preparation process 10, the compound of the following formula (Vb''') can be prepared by condensation reaction accompanied with dehydration and cyclization reaction of Compound (Vb5) and Compound (Vb6).

Wherein $R^4$, $R^5$, $Q^1$, $Q^2$, and n are as defined in Item 1.

Compound (IIc') can be prepared from Compound (IIc1) and Compound (IIc2) by the process of Preparation process 6.

Preparation Process 15

In Compound (IIc) which is used in the above Preparation process 3, the compound of the following formula (IIc") can be prepared by condensation reaction accompanied with dehydration and cyclization reaction of Compound (IIc3) and Compound (IIc4).

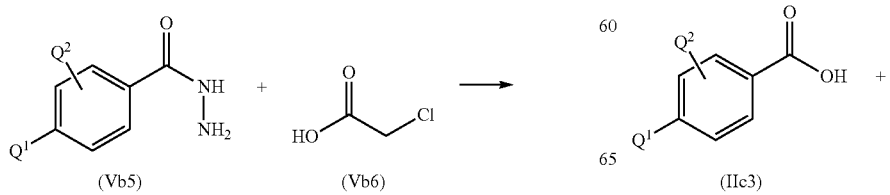

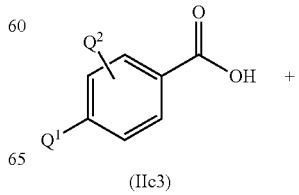

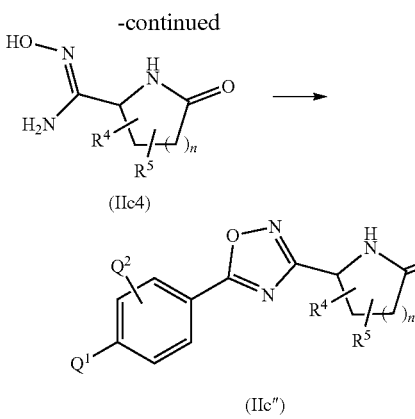

(IIc")

Wherein $R^4$, $R^5$, $Q^1$, $Q^2$, and n are as defined in Item 1.

Compound (IIc") can be prepared from Compound (IIc3) and Compound (IIc4) by the process of Preparation process 6.

Preparation Process 16

In Compound (IIc) which is used in the above Preparation process 3, the compound of the following formula (IIc''') can be prepared by condensation reaction accompanied with dehydration and cyclization reaction of Compound (IIc5) and Compound (IIc6).

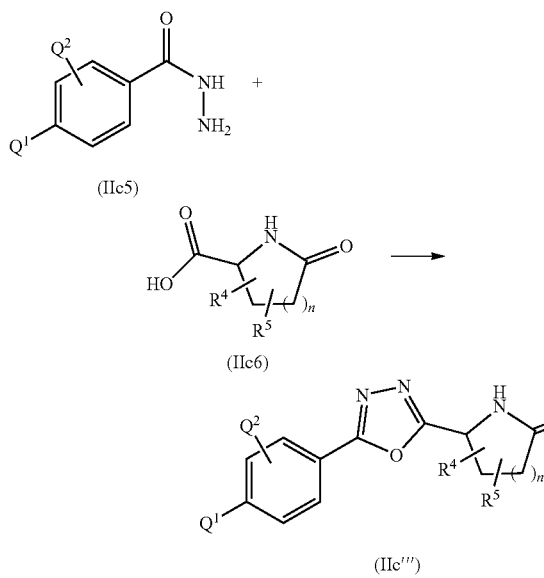

(IIc''')

Wherein $R^4$, $R^5$, $Q^1$, $Q^2$, and n are as defined in Item 1.

Compound (IIc''') can be prepared from Compound (IIc5) and Compound (IIc6) by the process of Preparation process 9.

The present compounds of formula (1) and their intermediates can be isolated and purified in a manner known by a skilled person. It includes, for example, extraction, partition, reprecipitation, column chromatography (e.g. silica gel column chromatography, ion exchange column chromatography, and preparative liquid chromatography), and recrystallization.

The solvent for recrystallization used herein includes, for example, an alcohol solvent such as methanol, ethanol, and 2-propanol; an ether solvent such as diethyl ether; an ester solvent such as ethyl acetate; an aromatic hydrocarbon solvent such as benzene and toluene; a ketone solvent such as acetone; a halogenated solvent such as dichloromethane and chloroform; a hydrocarbon solvent such as hexane; an aprotic solvent such as dimethylformamide and acetonitrile; water; and a mixed solvent thereof. As other methods for purification, for example, methods described in Series of Experimental Chemistry, Vol. 1 or other volumes (Jikken Kagaku Kouza, edited by the Chemical Society of Japan, issued by MARUZEN) can be used. And, the structure of the present compounds can be easily determined by spectroscopic analytical method such as nuclear magnetic resonance method, infrared absorption technique, and circular dichroism spectra analysis, and mass spectrometry, considering the structure of each starting compound.

In addition, each intermediate or each final product in the above preparation processes can be also transformed to another compound of the present invention by suitably modifying its functional group, especially extending various side-chains from amine, hydroxy, carbonyl, halogen, etc.; and optionally making the above-mentioned protection and deprotection if necessary. The modification of functional group and the extension of side-chain can be performed by a conventional method (for example, see Comprehensive Organic Transformations, R. C. Larock, John Wiley & Sons Inc. (1999), etc.).

The present compounds of formula (1) or a pharmaceutically acceptable salt thereof are sometimes asymmetric compounds or sometimes have a substituent including an asymmetric carbon. In such case, the compounds have optical isomers. The present compounds include a mixture of these isomers and an isolated one, which can be prepared in a conventional manner. The compounds having an asymmetric structure can be prepared, for example, by using a starting material having an asymmetric center or by introducing an asymmetric structure anywhere along the process. For example, in case of optical isomers, optical isomers can be obtained by using an optically active starting material or resolving a mixture of optical isomers at an appropriate step. In case that the compound of formula (1) or its intermediate has a basic functional group, the optical resolution thereof includes, for example, diastereomer method, wherein the compound is transformed to a salt thereof by reacting with an optically active acid (for example, a monocarboxylic acid such as mandelic acid, N-benzyloxyalanine, and lactic acid; dicarboxylic acid such as tartaric acid, o-diisopropylidenetartaric acid, and malic acid; or a sulfonic acid such as camphorsulfonic acid and bromocamphorsulfonic acid), in an inert solvent (for example, an alcohols such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof). In case that the compound of formula (1) or its intermediate has an acidic functional group such as carboxyl group, the compound can be also optically resolved by forming its salt with an optically active amine (for example, an organic amine such as 1-phenylethylamine, kinin, quinidine, cinchonidine, cinchonine, and strychnine).

The temperature for forming a salt is selected from the range of generally −50° C. to boiling point of a solvent used herein, preferably 0° C. to the boiling point, and more preferably room temperature to the boiling point. In order to enhance the optical purity, it is desirable to make the temperature raised to around boiling point of a solvent used herein. In collecting a precipitated crystal on a filter, an optional cooling can make the yield increased. The amount of an optically active acid or amine used herein is suitably about 0.5-about 2.0 equivalents against that of the substance compound, preferably around one equivalent. If appropriate, the obtained crystal may be recrystallized in an inert solvent (for example, an alcohol such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof) to obtain its highly pure salt thereof. And, if appropriate, the optically-resolved salt can be also treated with an acid or a base to obtain its free form.

Among the starting materials and the intermediates in each preparation process mentioned above, the compounds that are not described in each process are commercially available or can be prepared by a skilled person with a commercial available material in a known manner or a similar manner thereto.

The novel oxadiazole derivative of the present invention has anticonvulsive effect and the potentiating effect on GABA(A) receptors (activation of GABAergic system), thus the derivative may be a medicament for treating and/or preventing diseases associated with hypofunction of GABAergic system. In addition, the novel oxadiazole derivative of the present invention has the potentiating effect on GABA(A) receptors, and/or an effect for increasing inhibition (I) in balance of excitation (E) and inhibition (I) (E/I balance), thus the derivative may be a medicament for treating and/or preventing neurological disease or psychiatric disease. The neurological disease or psychiatric disease includes epilepsy such as epileptic seizure (tonic seizure, clonic seizure, absence seizure, myoclonic seizure, generalized seizure including atonic seizure, focal seizure, an unknown seizure), status epilepticus, West syndrome, Dravet syndrome, Lennox-Gastaut syndrome, autosomal dominant nocturnal frontal lobe epilepsy (ADNFLE), mesial temporal lobe epilepsy associated with hippocampal sclerosis which is a definitely identified symptom, and Rasmussen syndrome; neuropathic pain; developmental disorder; autism; bipolar disorder; schizophrenia; Alzheimer's disease and the other dementia; amyotrophic lateral sclerosis; Parkinson's disease; depressive symptom accompanying or unaccompanying epilepsy; anxiety disorder; obsessive-compulsive disorder; and REM sleep behavior disorder associated with Parkinson's disease/dementia with Lewy bodies. The novel oxadiazole derivative of the present invention may be a medicament for treating and/or preventing, preferably epilepsy such as epileptic seizure (tonic seizure, clonic seizure, absence seizure, myoclonic seizure, generalized seizure including atonic seizure, focal seizure, an unknown seizure), status epilepticus, West syndrome, Dravet syndrome, Lennox-Gastaut syndrome, autosomal dominant nocturnal frontal lobe epilepsy (ADNFLE), mesial temporal lobe epilepsy associated with hippocampal sclerosis which is a definitely identified symptom, and Rasmussen syndrome.

In the present invention, the "prevention/preventing" means that the active ingredient of the present invention is administered to a healthy subject who does not suffer from the disease, for example, said purpose of the administration is for preventing the onset of the disease. The "treatment/treating" means that the active ingredient of the present invention is administered to a subject who is diagnosed with the disease by a physician (i.e., a patient). The administration to a patient suffering from the disease for inhibiting seizure associated with the disease is included in the "prevention/preventing" or "treatment/treating".

The novel oxadiazole derivative of the present invention has the potentiating effect on GABA(A) receptors, and/or an effect for increasing inhibition (I) in balance of excitation (E) and inhibition (I) (E/I balance), thus the derivative may be a medicament for treating and/or preventing neurological disease or psychiatric disease.

In addition, the novel oxadiazole derivative of the present invention may be a medicament for treating and/or preventing a disease in which excitation (E) is increased and/or inhibition (I) is decreased in E/I balance.

The neurological disease or psychiatric disease includes epilepsy, neuropathic pain, neurodevelopmental disorders, bipolar and related disorders, schizophrenia spectrum disorder, Alzheimer's disease and the other neurocognitive disorders, amyotrophic lateral sclerosis, Parkinson's disease, depressive syndrome, anxiety disorders, obsessive-compulsive disorder, trauma- and stressor-related disorders, sleep-wake disorders, and/or REM sleep behavior disorder associated with Parkinson's disease/dementia with Lewy bodies.

The novel oxadiazole derivative of the present invention has anticonvulsant effect and the potentiating effect on GABA(A) receptors (activation of GABAergic system), thus the derivative may be a medicament for treating and/or preventing diseases associated with hypofunction of GABAergic system.

The diseases associated with hypofunction of GABAergic system include epilepsy, neuropathic pain, neurodevelopmental disorders, bipolar and related disorders, schizophrenia spectrum disorder, Alzheimer's disease and the other neurocognitive disorders, amyotrophic lateral sclerosis, Parkinson's disease, depressive syndrome, anxiety disorders, obsessive-compulsive disorder, trauma- and stressor-related disorders, sleep-wake disorders, and/or REM sleep behavior disorder associated with Parkinson's disease/dementia with Lewy bodies.

The epilepsy includes, for example, epileptic seizure (tonic seizure, clonic seizure, absence seizure, myoclonic seizure, generalized seizure including atonic seizure, focal seizure, an unknown seizure), status epilepticus, West syndrome, Dravet syndrome, Lennox-Gastaut syndrome, autosomal dominant nocturnal frontal lobe epilepsy (ADNFLE), Angelman syndrome, tuberous sclerosis, mesial temporal lobe epilepsy associated with hippocampal sclerosis which is a definitely identified symptom, and/or Rasmussen syndrome. The present invention may be preferably used in the treatment of particularly Dravet syndrome, Lennox-Gastaut syndrome, and/or Angelman syndrome.

The depressive syndrome includes, for example, depressive disorders with anxious distress, depressive disorders with mixed features, depressive disorders with melancholic features, depressive disorders with atypical features, depressive disorders with mood-congruent psychotic features, depressive disorders with mood-incongruent psychotic features, depressive disorders with catatonia, peripartum onset, seasonal depressive disorders, disruptive mood dysregulation disorder, depression/major depressive disorder, persistent depressive disorder, premenstrual dysphoric disorder, substance/medication-induced depressive disorder, depressive disorder due to another medical condition, other specified depressive disorder, and/or unspecified depressive disorder. In particular, it is preferable to be used for depression/major depressive disorder.

The anxiety disorders include, for example, separation anxiety disorder, selective mutism, specific phobia, social anxiety disorder, panic disorder, panic attack, agoraphobia, generalized anxiety disorder, substance/medication-induced anxiety disorder, anxiety disorder due to another medical condition, other specified anxiety disorder, and/or unspecified anxiety disorder.

The bipolar and related disorders include, for example, bipolar I disorder, bipolar II disorder, cyclothymic disorder, substance/medication-induced bipolar disorder and its related disorders, bipolar and its related disorders due to another medical condition, other specified bipolar and related disorders, and/or unspecified bipolar and related disorders. These disorders further include depressive symptom, depressive state, or anxiety symptom which is associated with the above-mentioned bipolar and related disorders.

In the present invention, the "prevention/preventing" means that the active ingredient of the present invention is administered to a healthy subject who does not suffer from the disease, for example, said purpose of the administration is for preventing the onset of the disease. The "treatment/treating" means that the active ingredient of the present invention is administered to a subject who is diagnosed with the disease by a physician (i.e., a patient). The administration to a patient suffering from the disease for inhibiting seizure associated with the disease is included in the "prevention/preventing" or "treatment/treating".

The present compounds may be administered orally, parenterally or rectally, and the daily dose can vary depending on the compound, the mode of administration, patient's condition/age, etc. For oral administration, for example, the present compounds may be administered generally in a dosage of about 0.01 to 1000 mg, preferably about 0.1 to 500 mg a day per kilogram of body weight of human or mammal and once to several times. For parenteral administration such as intravenous injection, for example, the present compounds may be administered generally in a dosage of about 0.01 to 300 mg, preferably about 1 to 100 mg per kilogram of body weight of human or mammal.

The present compounds can be orally or parenterally administered directly or as a suitable formulation comprising it. The formulation thereof may be, for example, tablet, capsule, powder, granule, liquid, suspension, injection, patch, gel patch, and the like, but not limited thereto. The formulation can be prepared with pharmaceutically acceptable additive agents in known means.

The additive agents can be chosen for any purpose, which include an excipient, a disintegrant, a binder, a fluidizer, a lubricant, a coating agent, a solubilizer, a solubilizing agent, a thickener, dispersant, a stabilizing agent, a sweetening agent, a flavor, and the like. Specifically, they include, for example, lactose, mannitol, microcrystalline cellulose, low-substituted hydroxypropylcellulose, cornstarch, partially-pregelatinized starch, carmellose calcium, croscarmellose sodium, hydroxypropylcellulose, hydroxypropyl methylcellulose, polyvinyl alcohol, magnesium stearate, sodium stearyl fumarate, polyethylene glycol, propylene glycol, titanium oxide, talc, and the like.

The present compounds may be used in combination with at least one other drug selected from drugs classified into antiepileptic drug, antidepressant drug, or antipsychotic drug. The combination with another drug here means that the other drug is formulated separately from the present compound, and the formulation comprising the other drug may be administered to a subject at the same time as the formulation comprising the present compound or in a time interval with the formulation comprising the present compound. The drug classified into antiepileptic drug includes, for example, phenytoin, valproic acid, carbamazepine, lamotrigine, topiramate, etc. which can inhibit sodium channel; ethosuximide, zonisamide, etc. which can inhibit calcium channel; perampanel which can inhibit AMPA receptor; a benzodiazepine which can enhance the activity of GABAergic system (such as diazepam, clonazepam, and clobazam); a barbiturate drug (such as phenobarbital); gabapentin; and vigabatrin. The drug classified into antidepressant drug includes, for example, fluoxetine, fluvoxamine, paroxetine, sertraline, citalopram, etc. which are referred to as SSRI; duloxetine, milnacipran, etc. which are referred to as SNRI; and imipramine, amitriptyline, clomipramine, amoxapine, etc. which are referred to as tricyclic antidepressant. The drug classified into antipsychotic drug includes, for example, haloperidol, spiperone, chlorpromazine, etc. which are referred to as typical antipsychotic; and risperidone, quetiapine, olanzapine, clozapine, perospirone, aripiprazole, etc. which are referred to as SDA.

EXAMPLES

The present invention is explained in more detail in the following by referring to Reference examples, Examples, and Tests; however, the technical scope of the present invention is not limited thereto. The compound names used herein are not always based on IUPAC nomenclature system.

In order to simplify description, abbreviations shown below may be sometimes used in Reference examples, Examples, and Tables in Examples. Me: methyl, Ph: phenyl, THF: tetrahydrofuran, DMF: N,N-dimethylformamide, DME: 1,2-dimethoxyethane, DMSO: dimethylsulfoxide, TFA: trifluoroacetic acid, MeCN: acetonitrile, n-: normal-, t-: tert-. The symbols used in NMR are defined as follows, s: singlet, d: doublet, dd: doublet of doublet, t: triplet, td: triplet of doublet, q: quartet, m: multiplet, br: broad, brs: broad singlet, brm: broad multiplet, and J: coupling constant.

Liquid Chromatography-Mass Spectrometry; Analytical conditions of LC/MS are shown below. Observed mass spectrometry value [MS(m/z)] is shown in MH$^+$, and retention time is shown as Rt (minutes).
Detection apparatus: Waters ACQUITY™ UltraPerformance LC Column: ACQUITY UPLC BEH C18 1.7 μm 2.1×30 mm column
Solvent: A: 0.05% HCOOH/H$_2$O, B: CH—CN
Gradient Condition:
  0.0-1.3 minutes; A/B=90/10-5/95 (linear gradient)
  1.3-1.5 minutes; A/B=90/10
Flow rate: 0.80 mL/min
UV: 220 nm, 254 nm
Column temperature: 40° C.

Reference Example 1: Ethyl 1-[3-(4-chlorophenyl)-1,2,4-oxadiazol-5-yl]cyclobutane-1-carboxylate

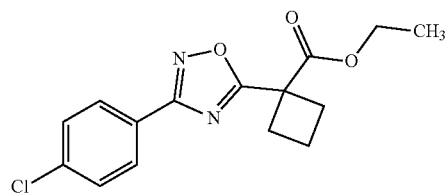 [SMILES: CCOC(=O)C1(c2nc(-c3ccc(Cl)cc3)no2)CCC1]

To cyclobutane-1,1-dicarboxylic acid monoethyl ester (100 mg) was added thionyl chloride (93 μl), and the mixture was refluxed for 5 hours. The reaction mixture was concentrated under reduced pressure, and then the residue was azeotropically dried with toluene to give ethyl 1-(chlorocarbonyl)cyclobutane-1-carboxylate as an oil. The oily product was dissolved in acetone (2.64 ml). To the solution were added 4-chlorobenzamidoxime (90 mg) and potassium carbonate (109 mg), and the mixture was stirred at 50° C. for an hour. The solid in the reaction mixture was removed by filtration and the filtrate was concentrated. The residue was dissolved in toluene (2.64 ml), and the solution was refluxed for 6 hours. The solvent was removed under reduced pressure, and the residue was purified by silica gel column chromatography (n-hexane:ethyl acetate; 6:1) to give Reference example 1 (138 mg) as a solid.

$^1$H-NMR (CDCl$_3$) δ: 1.25 (t, 3H), 2.08-2.23 (m, 2H), 2.76-2.84 (m, 2H), 2.86-2.94 (m, 2H), 4.24 (q, 2H), 7.45-7.48 (m, 2H), 8.04-8.07 (m, 2H).

Reference Examples 2-11

Each compound shown in Table 1 was prepared from each corresponding starting compound in a similar reaction and treatment to the method described in Reference example 1.

TABLE 1

| Reference example | Structure |
|---|---|
| 2 | (3-(4-fluorophenyl)-1,2,4-oxadiazol-5-yl)-2-methylpropanoate methyl ester |
| 3 | (3-(4-chlorophenyl)-1,2,4-oxadiazol-5-yl)-2-methylpropanoate methyl ester |
| 4 | (3-(4-bromophenyl)-1,2,4-oxadiazol-5-yl)-2-methylpropanoate methyl ester |
| 5 | 1-(3-(4-fluorophenyl)-1,2,4-oxadiazol-5-yl)cyclopropanecarboxylate methyl ester |
| 6 | 1-(3-(4-chlorophenyl)-1,2,4-oxadiazol-5-yl)cyclopropanecarboxylate methyl ester |
| 7 | isopropyl 3-fluoro-1-(3-(4-chlorophenyl)-1,2,4-oxadiazol-5-yl)cyclobutanecarboxylate |
| 8 | ethyl 3,3-difluoro-1-(3-(4-chlorophenyl)-1,2,4-oxadiazol-5-yl)cyclobutanecarboxylate |
| 9 | ethyl 1-(3-(4-chlorophenyl)-1,2,4-oxadiazol-5-yl)cyclopentanecarboxylate |
| 10 | ethyl 4-(3-(4-fluorophenyl)-1,2,4-oxadiazol-5-yl)tetrahydro-2H-pyran-4-carboxylate |
| 11 | ethyl 2-(3-(4-chlorophenyl)-1,2,4-oxadiazol-5-yl)-2-ethylbutanoate |

Reference Example 12: Ethyl 2-[5-(4-chlorophenyl)-1,2,4-oxadiazol-3-yl]acetate

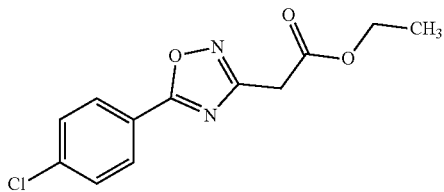 [SMILES: CCOC(=O)Cc1noc(-c2ccc(Cl)cc2)n1]

To a solution of ethyl 3-(hydroxyamino)-3-iminopropionate (4.00 g) in pyridine (40 ml) was added 4-chlorobenzoyl chloride (3.48 ml), and the mixture was stirred at room temperature for 2 hours. The reaction solution was further stirred at 90° C. for 20 hours, and then concentrated under reduced pressure. The residue was dissolved in ethyl acetate, washed with 10% aqueous citric acid and brine, and dried over anhydrous sodium sulfate. The solvent was removed under reduced pressure from the solution. The residue was purified by silica gel column chromatography (n-hexane:ethyl acetate; 2:1) to give Reference example 12 (4.60 g) as a solid.

$^1$H-NMR (CDCl$_3$) δ: 1.28 (t, 3H), 3.86 (s, 2H), 4.23 (q, 2H), 7.49 (d, 2H), 8.05 (d, 2H).

Reference Examples 13-14

Each compound shown in Table 2 was prepared from each corresponding starting compound in a similar reaction and treatment to the method described in Reference example 12.

TABLE 2

| Reference example | Structure |
|---|---|
| 13 | 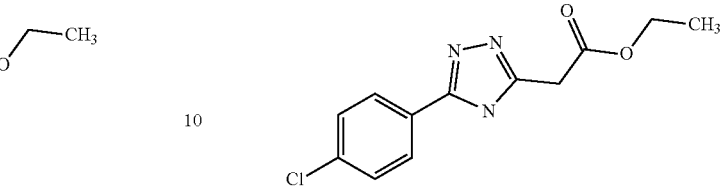 |
| 14 | 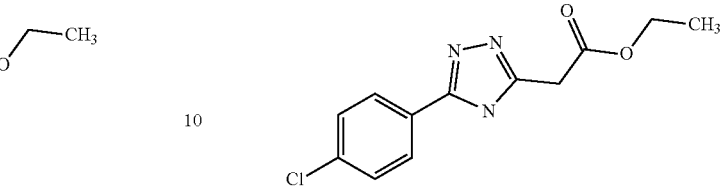 |

Reference Example 15: Ethyl 2-[5-(4-chlorophenyl)-1,3,4-oxadiazol-2-yl]acetate

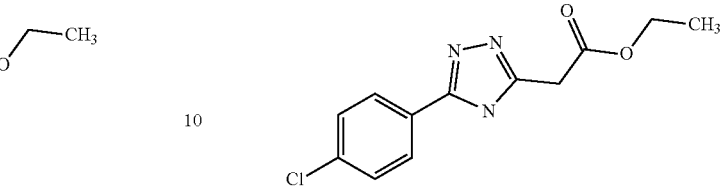

To a suspension of 4-chlorobenzhydrazide (500 mg) and ethyl malonyl chloride (0.37 ml) in THF (10 ml) was added triethylamine (0.86 ml), and the mixture was stirred at room temperature for 2 hours and then concentrated under reduced pressure. The obtained residue was dissolved in chloroform (10 ml), and Burgess reagent (1.54 g) was added to the solution. The mixture was refluxed for 6 hours, and concentrated under reduced pressure. The residue was purified by silica gel column chromatography (n-hexane:ethyl acetate; 2:1) to give Reference example 15 (598 mg) as a solid product.

$^1$H-NMR (CDCl$_3$) δ: 1.28 (t, 3H), 4.01 (s, 2H), 4.23 (q, 2H), 7.45-7.50 (m, 2H), 7.96-7.99 (m, 2H).

Reference Example 16

The compound of Reference example 16 was prepared from the corresponding starting compound in a similar reaction and treatment to the method described in Reference example 15.

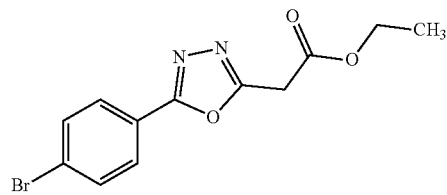 [SMILES: CCOC(=O)Cc1nnc(-c2ccc(Cl)cc2)[nH]1]

Reference Example 17: Ethyl 2-[5-(4-chlorophenyl)-1,2,4-oxadiazol-3-yl]-2-methylpropanoate

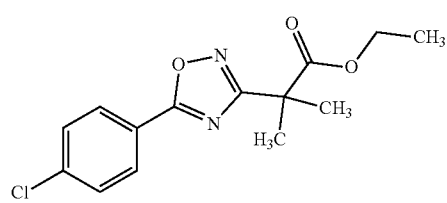 [SMILES: CCOC(=O)C(C)(C)c1noc(-c2ccc(Cl)cc2)n1]

To a solution of the compound of Reference example 12 (1.60 g) in DMF (16 ml) were added cesium carbonate (7.82 g) and methyl iodide (1.12 ml), and the mixture was stirred at room temperature overnight. To the reaction solution was added water, and the mixture was extracted with ethyl acetate. The organic layer was washed with brine, and dried over anhydrous sodium sulfate. The solvent was removed under reduced pressure. The residue was purified by silica gel column chromatography (n-hexane:ethyl acetate; 9:1) to give Reference example 17 (1.11 g) as a solid.

¹H-NMR (CDCl₃) δ: 1.21 (t, 3H), 1.67 (s, 6H), 4.17 (q, 2H), 7.47-7.50 (m, 2H), 8.04-8.07 (m, 2H).

Reference Examples 18-21

Each compound shown in Table 3 was prepared from each corresponding starting compound in a similar reaction and treatment to the method described in Reference example 17.

TABLE 3

| Reference example | Structure |
|---|---|
| 18 | 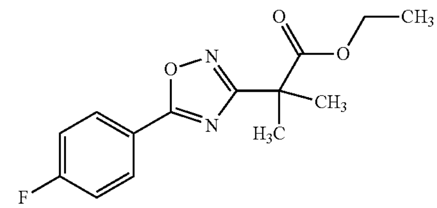 [SMILES: CCOC(=O)C(C)(C)c1noc(-c2ccc(F)cc2)n1] |
| 19 | 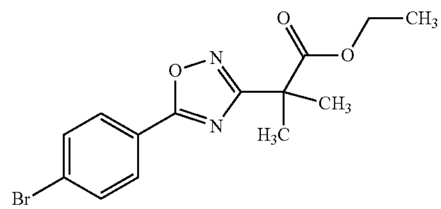 [SMILES: CCOC(=O)C(C)(C)c1noc(-c2ccc(Br)cc2)n1] |
| 20 | 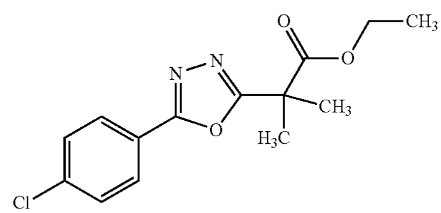 [SMILES: CCOC(=O)C(C)(C)c1nnc(-c2ccc(Cl)cc2)o1] |
| 21 | 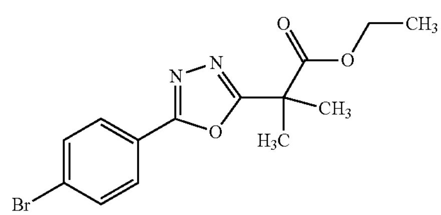 [SMILES: CCOC(=O)C(C)(C)c1nnc(-c2ccc(Br)cc2)o1] |

Reference Example 22: 2-[3-(4-Chlorophenyl)-1,2,4-oxadiazol-5-yl]-2-methylpropanoic acid

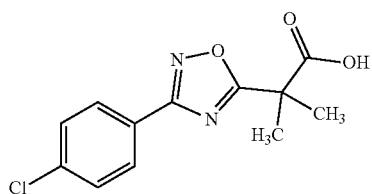 [SMILES: CC(C)(C(=O)O)c1nc(-c2ccc(Cl)cc2)no1]

To a solution of the compound of Reference example 3 (3.10 g) in methanol (20 ml) was added 5 mol/L aqueous sodium hydroxide (7.3 ml), and the mixture was refluxed for 6 hours. The reaction solution was cooled to room temperature, and then 10% aqueous citric acid was added to the solution to adjust the pH to pH 4. The solution was extracted with ethyl acetate. The organic layer was washed with brine, and dried over anhydrous sodium sulfate. The solvent was removed under reduced pressure to give Reference example 22 (2.89 g) as a solid product.

¹H-NMR (CDCl₃) δ: 1.78 (s, 6H), 7.42-7.46 (m, 2H), 8.00-8.03 (m, 2H).

Reference Examples 23-37

Each compound shown in Table 4 was prepared from each corresponding starting compound in a similar reaction and treatment to the method described in Reference example 22.

TABLE 4

| Reference example | Structure |
|---|---|
| 23 | 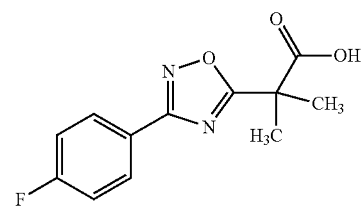 [SMILES: CC(C)(C(=O)O)c1nc(-c2ccc(F)cc2)no1] |
| 24 | 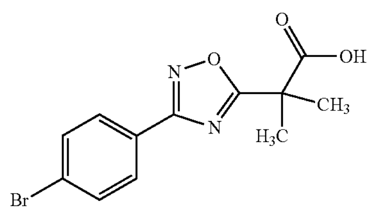 [SMILES: CC(C)(C(=O)O)c1nc(-c2ccc(Br)cc2)no1] |
| 25 | 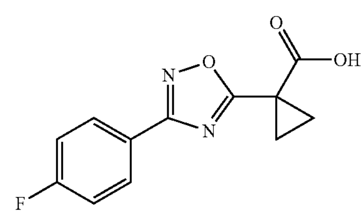 [SMILES: O=C(O)C1(c2nc(-c3ccc(F)cc3)no2)CC1] |
| 26 | 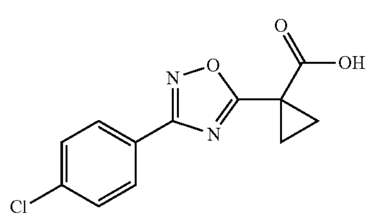 [SMILES: O=C(O)C1(c2nc(-c3ccc(Cl)cc3)no2)CC1] |
| 27 | 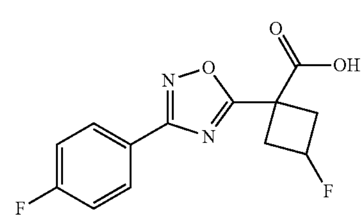 [SMILES: O=C(O)C1(c2nc(-c3ccc(F)cc3)no2)CC(F)C1] |

TABLE 4-continued

| Reference example | Structure |
|---|---|
| 28 | 3-(4-chlorophenyl)-1,2,4-oxadiazol-5-yl, 3,3-difluorocyclobutane-1-carboxylic acid |
| 29 | 3-(4-chlorophenyl)-1,2,4-oxadiazol-5-yl cyclobutane-1-carboxylic acid |
| 30 | 3-(4-chlorophenyl)-1,2,4-oxadiazol-5-yl cyclopentane-1-carboxylic acid |
| 31 | 3-(4-chlorophenyl)-1,2,4-oxadiazol-5-yl tetrahydropyran-4-carboxylic acid |
| 32 | 3-(4-chlorophenyl)-1,2,4-oxadiazol-5-yl, 2-ethyl-2-ethylbutanoic acid |
| 33 | 3-(4-fluorophenyl)-1,2,4-oxadiazol-5-yl, 2-methyl-2-methylpropanoic acid |
| 34 | 5-(4-chlorophenyl)-1,2,4-oxadiazol-3-yl, 2-methyl-2-methylpropanoic acid |
| 35 | 5-(4-bromophenyl)-1,2,4-oxadiazol-3-yl, 2-methyl-2-methylpropanoic acid |
| 36 | 2-(4-chlorophenyl)-1,3,4-oxadiazol-5-yl, 2-methyl-2-methylpropanoic acid |
| 37 | 2-(4-bromophenyl)-1,3,4-oxadiazol-5-yl, 2-methyl-2-methylpropanoic acid |

Reference Example 38: Sodium [3-(4-bromophenyl)-1,2,4-oxadiazol-5-yl]methanesulfonate To a solution of 3-(4-bromophenyl)-5-(chloromethyl)-1,2,4-oxadiazole (1.35 g) in ethanol (5 ml) was added a solution of sodium sulfite (0.62 g) in water (5 ml), and the mixture was refluxed for 4 hours. The solvent was removed under reduced pressure to give Reference example 38 (2.04 g) as a solid.

MS (m/z) 317 (MNa$^-$), Rt=0.52 min.

Reference Examples 39-45

Each compound shown in Table 5 was prepared from each corresponding starting compound in a similar reaction and treatment to the method described in Reference example 38.

TABLE 5

| Reference example | Structure |
|---|---|
| 39 | 3-(4-fluorophenyl)-1,2,4-oxadiazol-5-yl methanesulfonate sodium salt |
| 40 | 3-(4-chlorophenyl)-1,2,4-oxadiazol-5-yl methanesulfonate sodium salt |
| 41 | 5-(4-chlorophenyl)-1,2,4-oxadiazol-3-yl methanesulfonate sodium salt |
| 42 | 5-(4-bromophenyl)-1,2,4-oxadiazol-3-yl methanesulfonate sodium salt |
| 43 | 5-(4-fluorophenyl)-1,3,4-oxadiazol-2-yl methanesulfonate sodium salt |
| 44 | 5-(4-chlorophenyl)-1,3,4-oxadiazol-2-yl methanesulfonate sodium salt |
| 45 | 5-(4-bromophenyl)-1,3,4-oxadiazol-2-yl methanesulfonate sodium salt |

Reference Example 46: 1-[3-(4-Bromophenyl)-1,2,4-oxadiazol-5-yl]-N,N-bis(2,4-dimethoxybenzyl)methanesulfonamide

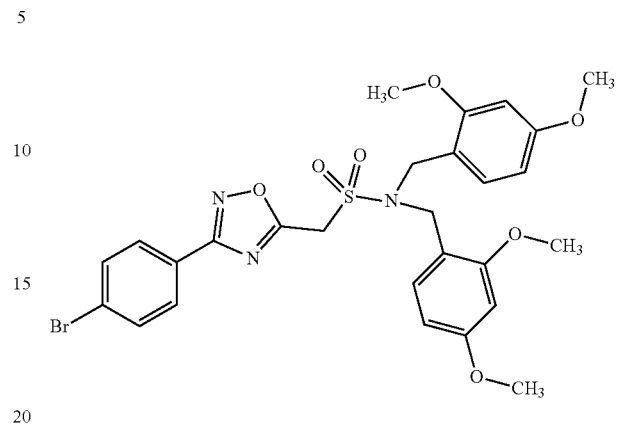

To the compound of Reference example 38 (1.68 g) was added phosphorus oxychloride (22.5 ml), and the mixture was refluxed for 5 hours and then concentrated under reduced pressure. The residue was dissolved in THF (20 ml), and the solution was added dropwise to a solution of bis(2,4-dimethoxybenzyl)amine (1.56 g), triethylamine (2.75 ml), and 4-dimethylaminopyridine (0.06 g) in THF (20 ml). The solution was stirred at room temperature overnight. The reaction solution was diluted with 10% aqueous citric acid, and extracted with ethyl acetate. The organic layer was washed with brine, and dried over anhydrous sodium sulfate. The solvent was removed under reduced pressure. The residue was purified by silica gel column chromatography (n-hexane:ethyl acetate; 2:1) to give Reference example 46 (1.32 g) as an amorphous.

$^1$H-NMR (CDCl$_3$) δ: 3.78 (s, 12H), 4.38 (s, 2H), 4.38 (s, 4H), 6.43-6.46 (m, 4H), 7.20 (d, 2H), 7.58-7.61 (m, 2H), 7.89-7.93 (m, 2H).

Reference Examples 47-53

Each compound shown in Table 6 was prepared from each corresponding starting compound in a similar reaction and treatment to the method described in Reference example 46.

TABLE 6

| Reference example | Structure |
|---|---|
| 47 | 1-[3-(4-fluorophenyl)-1,2,4-oxadiazol-5-yl]-N,N-bis(2,4-dimethoxybenzyl)methanesulfonamide |

TABLE 6-continued

| Reference example | Structure |
|---|---|
| 48 | [structure: 3-(4-chlorophenyl)-1,2,4-oxadiazol-5-yl methyl sulfonamide with N,N-bis(2,4-dimethoxybenzyl)] |
| 49 | [structure: 5-(4-chlorophenyl)-1,2,4-oxadiazol-3-yl methyl sulfonamide with N,N-bis(2,4-dimethoxybenzyl)] |
| 50 | [structure: 5-(4-bromophenyl)-1,2,4-oxadiazol-3-yl methyl sulfonamide with N,N-bis(2,4-dimethoxybenzyl)] |
| 51 | [structure: 5-(4-fluorophenyl)-1,3,4-oxadiazol-2-yl methyl sulfonamide with N,N-bis(2,4-dimethoxybenzyl)] |
| 52 | [structure: 5-(4-chlorophenyl)-1,3,4-oxadiazol-2-yl methyl sulfonamide with N,N-bis(2,4-dimethoxybenzyl)] |
| 53 | [structure: 5-(4-bromophenyl)-1,3,4-oxadiazol-2-yl methyl sulfonamide with N,N-bis(2,4-dimethoxybenzyl)] |

Reference Example 54: 2-[3-(4-Bromophenyl)-1,2,4-oxazol-5-yl]-N,N-bis(2,4-dimethoxybenzyl)propane-2-sulfonamide

[structure of Reference Example 54]

To a solution of the compound of Reference example 46 (250 mg) in DMF (5 ml) were added cesium carbonate (527 mg) and methyl iodide (0.075 ml), and the mixture was stirred at room temperature overnight. To the reaction solution was added water, and the mixture was extracted with ethyl acetate. The organic layer was washed with brine, and dried over anhydrous sodium sulfate. The solvent was removed under reduced pressure from the solution. The residue was purified by silica gel column chromatography (n-hexane:ethyl acetate; 1:1) to give Reference example 54 (241 mg) as an amorphous.

$^1$H-NMR (CDCl$_3$) δ: 1.93 (s, 6H), 3.57 (s, 6H), 3.71 (s, 6H), 4.27 (br s, 4H), 5.43 (br s, 1H), 6.77 (br s, 1H), 7.14-7.19 (m, 2H), 8.05-8.10 (m, 2H).

Reference Examples 55-61

Each compound shown in Table 7 was prepared from each corresponding starting compound in a similar reaction and treatment to the method described in Reference example 54.

TABLE 7

| Reference example | Structure |
|---|---|
| 55 | 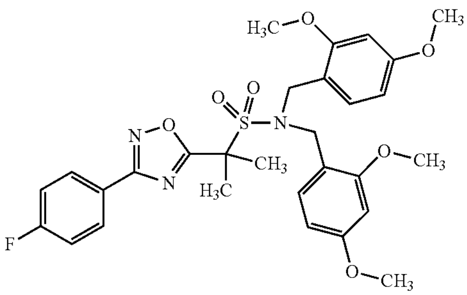 [SMILES: COc1ccc(CN(Cc2ccc(OC)cc2OC)S(=O)(=O)C(C)(C)c2nc(-c3ccc(F)cc3)no2)c(OC)c1] |
| 56 | 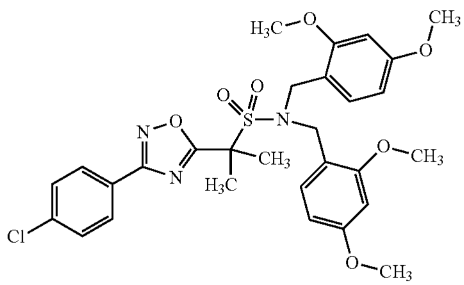 [SMILES: COc1ccc(CN(Cc2ccc(OC)cc2OC)S(=O)(=O)C(C)(C)c2nc(-c3ccc(Cl)cc3)no2)c(OC)c1] |
| 57 | 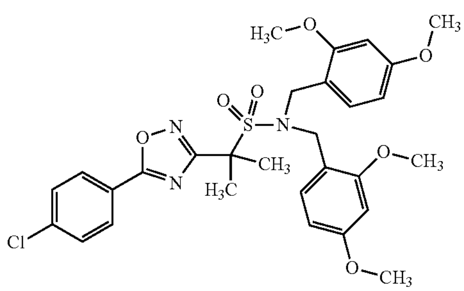 [SMILES: COc1ccc(CN(Cc2ccc(OC)cc2OC)S(=O)(=O)C(C)(C)c2noc(-c3ccc(Br)cc3)n2)c(OC)c1] |
| 58 | 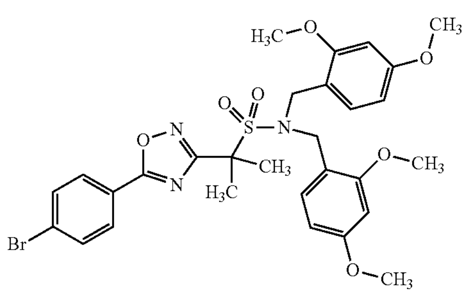 |
| 59 | 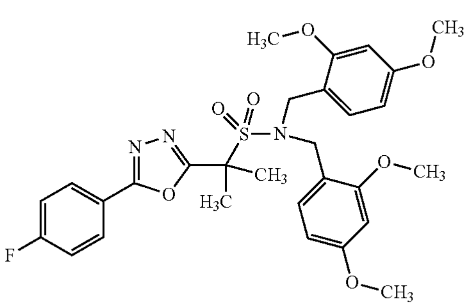 [SMILES: COc1ccc(CN(Cc2ccc(OC)cc2OC)S(=O)(=O)C(C)(C)c2nnc(-c3ccc(F)cc3)o2)c(OC)c1] |
| 60 | |
| 61 | |

Reference Example 62: 5-[3(4-Fluorophenyl)-1,2,4-oxadiazol-5-yl]pyrrolidin-2-one

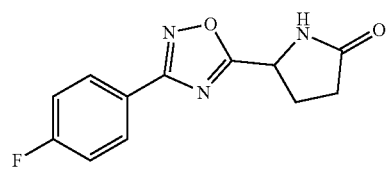 [SMILES: O=C1CCC(c2nc(-c3ccc(F)cc3)no2)N1]

To a solution of 4-fluorobenzamidoxime (1.90 g), 2-pyrrolidone-5-carboxylic acid (1.59 g), and O-(7-azabenzotriazol-1-yl)-N,N,N',N'-tetramethyluronium hexafluorophosphate (5.16 g) in DME (50 ml) was added N,N-diisopropylethylamine (4.3 ml), and the mixture was stirred at room temperature for 2 hours and then at 80° C. for 2 hours. To the reaction solution was added water, and the mixture was extracted with ethyl acetate. The organic layer was washed with brine, and dried over anhydrous sodium sulfate. The solvent was removed under reduced pressure from the solution. The residue was purified by silica gel column chromatography (n-hexane:ethyl acetate; 1:4) to give Reference example 62 (2.30 g) as a solid.

$^1$H-NMR (d6-DMSO) δ: 2.21-2.40 (m, 3H), 2.51-2.62 (m, 1H), 5.09-5.12 (m, 1H), 7.38-7.44 (m, 2H), 8.04-8.09 (m, 2H), 8.37 (br s, 1H).

Reference Examples 63-68

Each compound shown in Table 8 was prepared from each corresponding starting compound in a similar reaction and treatment to the method described in Reference example 62.

TABLE 8

| Reference example | Structure |
|---|---|
| 63 | 3-(2,4-difluorophenyl)-1,2,4-oxadiazol-5-yl pyrrolidinone |
| 64 | 3-(3,4-difluorophenyl)-1,2,4-oxadiazol-5-yl pyrrolidinone |
| 65 | 3-(4-fluorophenyl)-1,2,4-oxadiazol-5-yl (methyl)pyrrolidinone |
| 66 | 3-(4-chlorophenyl)-1,2,4-oxadiazol-5-yl pyrrolidinone |
| 67 | 3-(4-bromophenyl)-1,2,4-oxadiazol-5-yl pyrrolidinone |

TABLE 8-continued

| Reference example | Structure |
|---|---|
| 68 | 3-(4-fluorophenyl)-1,2,4-oxadiazol-5-yl pyrrolidinone |

Example 1: 2-[3-(4-Fluorophenyl)-1,2,4-oxadiazol-5-yl]-2-methylpropanamide

The compound of Reference example 23 (280 mg) and oxalyl chloride (0.384 ml) were dissolved in dry chloroform (10 ml), two drops of DMF were added to the solution, and the solution was stirred at room temperature for an hour. The reaction solution was concentrated under reduced pressure, and the obtained residue was dissolved in dry THF (5 ml). To the solution was added 28% aqueous ammonia solution (1 ml), and the mixture was stirred at room temperature overnight. The reaction solution was concentrated under reduced pressure, and the obtained residue was purified by silica gel column chromatography (n-hexane:ethyl acetate; 1:1) to give Example 1 (206 mg) as a solid.

$^1$H-NMR (CDCl) δ: 1.75 (s, 6H), 5.43 (br s, 1H), 6.77 (br s, 1H), 7.14-7.19 (m, 2H), 8.05-8.10 (m, 2H). MS (m/z) 250 (MH$^+$), Rt=0.69 min.

Examples 2-16

Each compound shown in Table 9 was prepared from each corresponding starting compound in a similar reaction and treatment to the method described in Example 1.

TABLE 9

| Example | Structure | $^1$H-NMR δ: | LC-MS [M + H]$^+$/Rt |
|---|---|---|---|
| 2 | 2-[3-(4-chlorophenyl)-1,2,4-oxadiazol-5-yl]-2-methylpropanamide | CDCl$_3$: 1.75 (s, 6H), 5.45 (br s, 1H), 6.74 (br s, 1H), 7.44-7.47 (m, 2H), 7.99-8.03 (m, 2H) | 266/0.80 min |

TABLE 9-continued

| Example | Structure | ¹H-NMR δ: | LC-MS [M + H]⁺/Rt |
|---|---|---|---|
| 3 | 3-(4-bromophenyl)-1,2,4-oxadiazol-5-yl with C(CH₃)₂C(O)NH₂ | CDCl₃: 1.77 (s, 6H), 5.49 (br s, 1H), 6.75 (br s, 1H), 7.62-7.65 (m, 2H), 7.94-7.98 (m, 2H) | 310/0.80 min |
| 4 | 3-(4-fluorophenyl)-1,2,4-oxadiazol-5-yl cyclopropane carboxamide | CDCl₃: 1.70-1.81 (m, 2H), 1.93-2.03 (m, 2H), 5.75 (br s, 1H), 7.10-7.15 (m, 2H), 7.97-8.02 (m, 2H), 8.89 (br s, 1H) | 248/0.74 min |
| 5 | 3-(4-chlorophenyl)-1,2,4-oxadiazol-5-yl cyclopropane carboxamide | CDCl₃: 1.75-1.86 (m, 2H), 1.98-2.08 (m, 2H), 5.80 (br s, 1H), 7.45-7.48 (m, 2H), 7.97-8.00 (m, 2H), 8.91 (br s, 1H) | 264/0.83 min |
| 6 | 3-(4-chlorophenyl)-1,2,4-oxadiazol-5-yl 3-fluorocyclobutane carboxamide | CDCl₃: 2.94-3.13 (m, 2H), 3.19-3.30 (m, 2H), 5.11-5.48 (m, 1H), 5.71 (br s, 1H), 6.78 (br s, 1H), 7.45-7.48 (m, 2H), 7.98-8.02 (m, 2H) | 296/0.82 min |
| 7 | 3-(4-chlorophenyl)-1,2,4-oxadiazol-5-yl 3,3-difluorocyclobutane carboxamide | CDCl₃: 3.28-3.39 (m, 2H), 3.54-3.67 (m, 2H), 5.64 (br s, 1H), 6.62 (br s, 1H), 7.46-7.50 (m, 2H), 7.99-8.03 (m, 2H) | 314/0.88 min |
| 8 | 3-(4-chlorophenyl)-1,2,4-oxadiazol-5-yl cyclobutane carboxamide | CDCl₃: 2.14-2.25 (m, 2H), 2.71-2.78 (m, 2H), 2.95-3.02 (m, 2H), 5.58 (br s, 1H), 6.74 (br s, 1H), 7.46-7.49 (m, 2H), 8.02-8.05 (m, 2H) | 278/0.81 min |
| 9 | 3-(4-chlorophenyl)-1,2,4-oxadiazol-5-yl cyclopentane carboxamide | CDCl₃: 1.70-1.81 (m, 2H), 1.85-1.95 (m, 2H), 2.42-2.56 (m, 4H), 5.44 (br s, 1H), 6.60 (br s, 1H), 7.44-7.47 (m, 2H), 7.99-8.03 (m, 2H) MS (m/z) 292 (MH+), Rt = 0.91 min. | 292/0.91 min |

TABLE 9-continued

| Example | Structure | ¹H-NMR δ: | LC-MS [M + H]⁺/Rt |
|---|---|---|---|
| 10 | 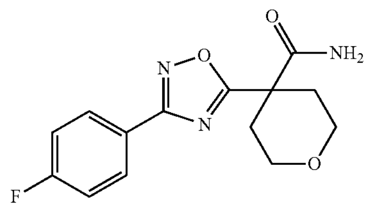 [SMILES: NC(=O)C1(c2nc(-c3ccc(F)cc3)no2)CCOCC1] | CDCl₃: 2.38-2.47 (m, 4H), 3.48-3.54 (m, 2H), 3.92-3.97 (m, 2H), 5.44 (br s, 1H), 6.01 (br s, 1H), 7.15-7.20 (m, 2H), 8.06-8.11 (m, 2H) | 308/0.66 min |
| 11 | 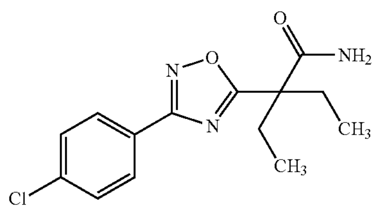 [SMILES: CCC(CC)(C(N)=O)c1nc(-c2ccc(Cl)cc2)no1] | CDCl₃: 0.80 (t, 6H), 2.03-2.12 (m, 2H), 2.24-2.33 (m, 2H), 5.78 (br s, 1H), 7.45-7.50 (m, 2H), 8.00-8.03 (m, 2H), 8.45 (br s, 1H) | 294/0.94 min |
| 12 | 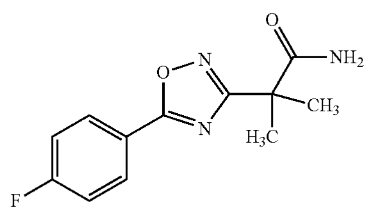 [SMILES: CC(C)(C(N)=O)c1noc(-c2ccc(F)cc2)n1] | CDCl₃: 1.70 (s, 6H), 5.47 (br s, 1H), 6.54 (br s, 1H), 7.18-7.24 (m, 2H), 8.12-8.17 (m, 2H) | 250/0.65 min |
| 13 | 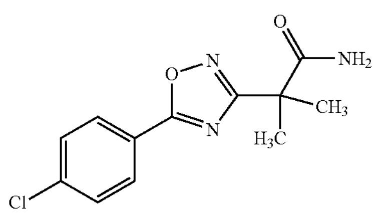 [SMILES: CC(C)(C(N)=O)c1noc(-c2ccc(Cl)cc2)n1] | CDCl₃: 1.70 (s, 6H), 5.40 (br s, 1H), 6.51 (br s, 1H), 7.49-7.52 (m, 2H), 8.05-8.08 (m, 2H) | 266/0.73 min |
| 14 | 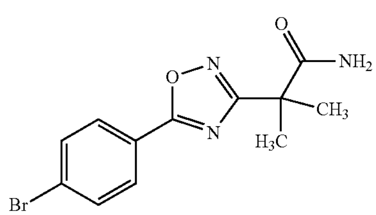 | CDCl₃: 1.72 (s, 6H), 5.46 (br s, 1H), 6.52 (br s, 1H), 7.69-7.71 (m, 2H), 8.00-8.02 (m, 2H) | 310/0.77 min |
| 15 | 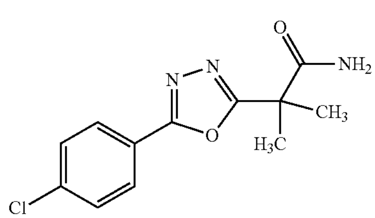 [SMILES: CC(C)(C(N)=O)c1nnc(-c2ccc(Cl)cc2)o1] | CDCl₃: 1.70 (s, 6H), 5.39 (br s, 1H), 6.57 (br s, 1H), 7.42-7.45 (m, 2H), 7.91-7.94 (m, 2H) | 266/0.62 min |
| 16 | 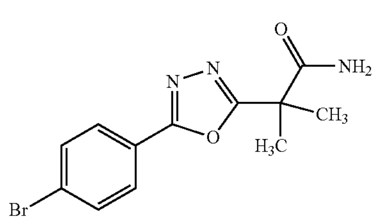 [SMILES: CC(C)(C(N)=O)c1nnc(-c2ccc(Br)cc2)o1] | CDCl₃: 1.74 (s, 6H), 5.56 (br s, 1H), 6.62 (br s, 1H), 7.63 (d, 2H), 7.88 (d, 2H) | 310/0.65 min |

Example 17: 2-[3-(4-Fluorophenyl)-1,2,4-oxadiazol-5-yl]propane-2-sulfonamide

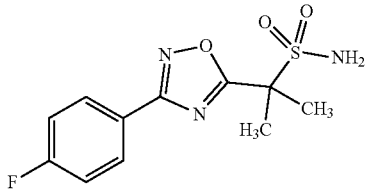 [SMILES: CC(C)(c1nc(-c2ccc(F)cc2)no1)S(N)(=O)=O]

To a solution of the compound of Reference example 55 in toluene (20 ml) was added trifluoroacetic acid (10 ml), and the mixture was stirred at room temperature for 15 hours. The reaction solution was concentrated under reduced pressure, and the obtained residue was purified by silica gel column chromatography (n-hexane:ethyl acetate; 1:1) to give Example 17 (103 mg) as a solid.

$^1$H-NMR (CDCl$_3$) δ: 1.98 (s, 6H), 4.95 (br s, 2H), 7.14-7.19 (m, 2H), 8.03-8.08 (m, 2H).

MS (m/z) 286 (MH$^+$), Rt=0.71 min.

Examples 18-24

Each compound shown in Table 10 was prepared from each corresponding starting compound in a similar reaction and treatment to the method described in Example 18.

TABLE 10

| Example | Structure | 1H-NMR (CDCl$_3$) δ | LC-MS [M + H]$^+$/Rt |
|---|---|---|---|
| 18 | 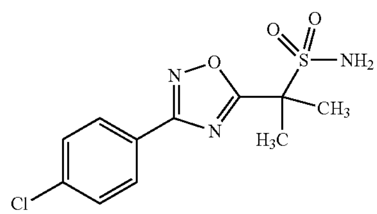 | 1.98 (s, 6H), 4.93 (br s, 2H), 7.44-7.47 (m, 2H), 7.98-8.01 (m, 2H) | 302/0.81 min |
| 19 | 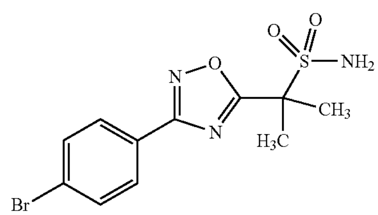 [SMILES: CC(C)(c1nc(-c2ccc(Cl)cc2)no1)S(N)(=O)=O] | 1.98 (s, 6H), 4.96 (br s, 2H), 7.61 (d, 2H), 7.92 (d, 2H) | 346/0.83 min |
| 20 | 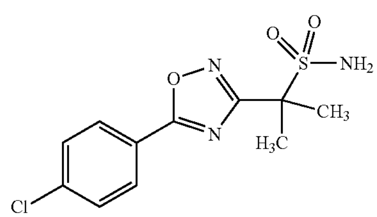 [SMILES: CC(C)(c1noc(-c2ccc(Cl)cc2)n1)S(N)(=O)=O] | 1.93 (s, 6H), 4.96 (br s, 2H), 7.50-7.53 (m, 2H), 8.03-8.07 (m, 2H) | 302/0.75 min |
| 21 | 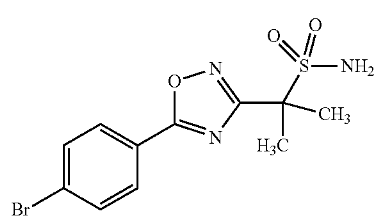 [SMILES: CC(C)(c1noc(-c2ccc(Br)cc2)n1)S(N)(=O)=O] | 1.95 (s, 6H), 4.98 (br s, 2H), 7.68-7.71 (m, 2H), 7.97-8.01 (m, 2H) | 346/0.87 min |
| 22 | 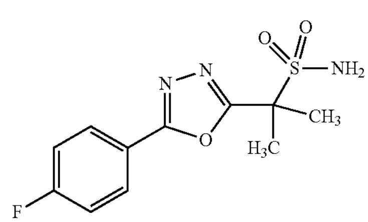 [SMILES: CC(C)(c1nnc(-c2ccc(F)cc2)o1)S(N)(=O)=O] | 2.01 (s, 6H), 4.87 (br s, 2H), 7.19-7.23 (m, 2H), 8.04-8.09 (m, 2H) | 286/0.57 min |

TABLE 10-continued

| Example | Structure | 1H-NMR (CDCl₃) δ | LC-MS [M + H]⁺/Rt |
|---|---|---|---|
| 23 | (structure: 5-(4-chlorophenyl)-1,3,4-oxadiazol-2-yl dimethyl sulfonamide) | 2.01 (s, 6H), 4.88 (br s, 2H), 7.48-7.52 (m, 2H), 7.97-8.00 (m, 2H) | 302/0.68 min |
| 24 | (structure: 5-(4-bromophenyl)-1,3,4-oxadiazol-2-yl dimethyl sulfonamide) | 1.98 (s, 6H), 4.99 (br s, 2H), 7.62 (d, 2H), 7.86 (d, 2H) | 346/0.68 min |

Example 25: 5-[3-(4-Fluorophenyl)-1,2,4-oxadiazol-5-yl]-1-methylpyrrolidin-2-one

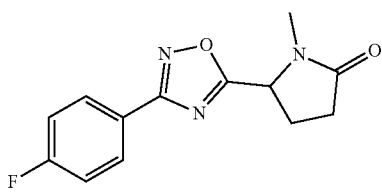 [SMILES: CN1C(=O)CCC1c1nc(-c2ccc(F)cc2)no1]

To a solution of the compound of Reference example 62 (500 mg) and methyl iodide (0.19 ml) in DMF (4 ml) was added cesium carbonate (0.988 g), and the mixture was stirred at room temperature for 2.5 hours. To the reaction solution was added 10% aqueous citric acid solution, and the mixture was extracted with ethyl acetate. The organic layer was washed with brine, and dried over anhydrous sodium sulfate. The organic layer was concentrated under reduced pressure, and the obtained residue was purified by silica gel column chromatography (n-hexane:ethyl acetate; 1:3) to give Example 25 (483 mg) as a solid.

¹H-NMR (CDCl₃) δ: 2.27-2.33 (m, 1H), 2.40-2.67 (m, 3H), 2.85 (s, 3H), 4.84-4.87 (m, 1H), 7.09-7.15 (m, 2H), 7.99-8.04 (m, 2H).

MS (m/z) 262 (MH⁺), Rt=0.71 min.

Examples 26-31

Each compound shown in Table 11 was prepared from each corresponding starting compound in a similar reaction and treatment to the method described in Example 25.

TABLE 11

| Example | Structure | ¹H-NMR(CDCl₃) δ | LC-MS [M + H]⁺/Rt |
|---|---|---|---|
| 26 | (structure: 3-(2,4-difluorophenyl)-1,2,4-oxadiazol-5-yl 1-methylpyrrolidin-2-one) | 2.27-2.34 (m, 1H), 2.41-2.67 (m, 3H), 2.85 (s, 3H), 4.87-4.90 (m, 1H), 6.91-7.00 (m, 2H), 7.98-8.04 (m, 1H) | 280/0.74 min |
| 27 | (structure: 3-(3,4-difluorophenyl)-1,2,4-oxadiazol-5-yl 1-methylpyrrolidin-2-one) | 2.31-2.38 (m, 1H), 2.45-2.71 (m, 3H), 2.89 (s, 3H), 4.89-4.92 (m, 1H), 7.26-7.32 (m, 1H), 7.82-7.86 (m, 1H), 7.87-7.86 (m, 1H) | 280/0.80 min |

TABLE 11-continued

| Example | Structure | ¹H-NMR(CDCl₃) δ | LC-MS [M + H]⁺/Rt |
|---|---|---|---|
| 28 | 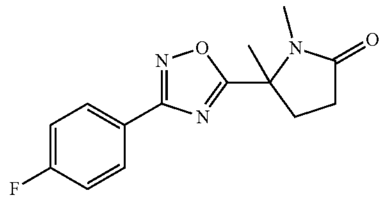 [SMILES: CN1C(=O)CCC1(C)c1nc(-c2ccc(F)cc2)no1] | 1.80 (s, 3H), 2.10-2.19 (m, 1H), 2.45-2.68 (m, 3H), 2.83 (s, 3H), 7.13-7.18 (m, 2H), 8.04-8.08 (m, 2H) | 276/0.82 min |
| 29 | 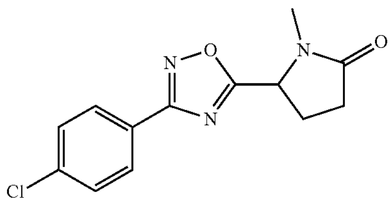 [SMILES: CN1C(=O)CCC1c1nc(-c2ccc(Cl)cc2)no1] | 2.27-2.33 (m, 1H), 2.40-2.67 (m, 3H), 2.84 (s, 3H), 4.84-4.87 (m, 1H), 7.39-7.42 (m, 2H), 7.94-7.97 (m, 2H) | 278/0.85 min |
| 30 | 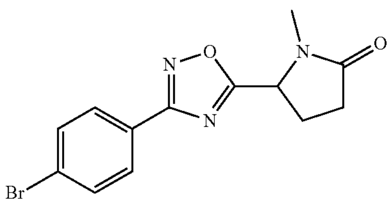 [SMILES: CN1C(=O)CCC1c1nc(-c2ccc(Br)cc2)no1] | 2.32-2.38 (m, 1H), 2.45-2.71 (m, 3H), 2.89 (s, 3H), 4.89-4.92 (m, 1H), 7.60-7.63 (m, 2H), 7.91-7.95 (m, 2H) | 322/0.87 min |
| 31 | 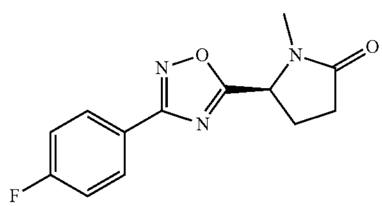 [SMILES: CN1C(=O)CC[C@H]1c1nc(-c2ccc(F)cc2)no1] | 2.27-2.33 (m, 1H), 2.40-2.67 (m, 3H), 2.85 (s, 3H), 4.84-4.87 (m, 1H), 7.09-7.15 (m, 2H), 7.99-8.04 (m, 2H) | 262/0.71 min |

Examples 31 and 32: (S)-5-[3-(4-Fluorophenyl)-1,2,4-oxadiazol-5-yl]-1-methylpyrrolidin-2-one and (R)-5-[3-(4-fluorophenyl)-1,2,4-oxadiazol-5-yl]-1-methylpyrrolidin-2-one

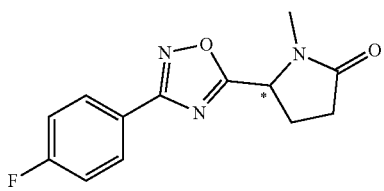 [SMILES: CN1C(=O)CCC1c1nc(-c2ccc(F)cc2)no1]

The compound prepared in Example 25 was separated with a DAICEL's column (CHIPALPAK™ AD-H (mobile phase: 100% MeCN)) to give the former peak (enantiomer A) and the latter peak (enantiomer B). The absolute configurations of enantiomers A and B were evaluated by comparing with the corresponding product prepared from Reference example 68 derived from the S-form starting compound (i.e., Example 31) to determine that enantiomer A is S form and enantiomer B is R form.

Example 31 (enantiomer A): Rt 4.78 minutes, Chiral HPLC (Chiralpak™ AD-H, 0.46 cm I.D.×25 cm L, mobile phase: 100% MeCN, flow rate: 1.0 ml/min, temperature: 40° C., wave length: 237 nm)

Example 32 (enantiomer B): Rt 5.99 minutes, Chiral HPLC (Chiralpak™ AD-H, 0.46 cm I.D.×25 cm L, mobile phase: 100% MeCN, flow rate: 1.0 ml/min, temperature: 40° C., wave length: 237 nm)

Example 33: (S)-5-[3-(4-Fluorophenyl)-1,2,4-oxadiazol-5-yl]-1-methylpyrrolidin-2-one

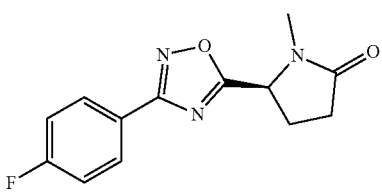 [SMILES: CN1C(=O)CC[C@H]1c1nc(-c2ccc(F)cc2)no1]

The compound of Example 31 can be also prepared in the manner below.

To a mixture of 4-fluorobenzamidoxime (840 g), (S)-2-pyrrolidone-5-carboxylic acid (1.08 kg), N,N-diisopropylethylamine (2.56 L), and ethyl acetate (7.3 L) was added a 50% solution of propylphosphonic anhydride in ethyl acetate (4.48 kg), and the mixture was stirred at room temperature for 1.5 hours and then at 75° C. for 2.5 hours. After the reaction solution was cooled to room temperature, 0.1 mol/L aqueous hydrochloric acid solution (3.36 L) was added to the reaction solution. The mixture was separated with a separatory funnel, and the aqueous layer was extracted with ethyl acetate (1.86 L) twice. The combined organic layer was washed with 5% aqueous dipotassium hydrogen phosphate solution (3.36 kg) and then water (1.68 L), and the organic layer was concentrated under reduced pressure to a weight of 3.36 kg. The concentrated solution was cooled to 0° C. with stirring. To the obtained slurry was added n-heptane (3.02 kg) dropwise, and the obtained crystal was collected on a filter, washed with 40% ethyl acetate/heptane (1.68 kg), and dried in vacuo at 40° C. to give a crude crystal (1.14 kg) as a pale brown solid. The obtained crude crystal (1.00 kg) was dissolved in 2-propanol/water (50%, 1.6 kg), and then 60 g of activated carbon was added thereto. The mixture was stirred at 25° C., and the activated carbon was removed by filtration. The filtrate was diluted with 2-propanol/water (50%) to adjust the total weight to 3.0 kg, and the diluted solution was added dropwise to water (6.0 L) at 0° C. with stirring. The obtained crystal was collected on a filter, washed with 2-propanol/water (12.5%, 2.0 kg), and dried in vacuo at 40° C. to give Example 33 (944 g) as a white solid. The data of NMR and HPLC showed that the present compound is identical to the compound of Example 31.

The results of pharmacological experiments with some typical compounds of the present invention are shown below and the pharmacological activities of the present compounds are also explained, but the scope of the present invention should not be limited thereto.

Test 1: Test with Model Produced by Subcutaneous Injection of Pentetrazol (Minimum Convulsion Model, scPTZ)

In order to evaluate an antiepileptic drug, in general, a model produced by subcutaneous injection of pentetrazol (minimum convulsion model, scPTZ) is used, which has high clinical predictability. A compound exhibiting an anticonvulsant action in the test with this model is expected to become an antiepileptic drug in clinical application. In this test, an animal model which expresses generalized absence seizure or myoclonic seizure was used. Test compounds were orally administered to Sic: ddY male mice (purchased from Japan SLC, Inc., 5 mice in each group, body weight 20-30 g). After an hour, pentetrazol (85 mg/kg) was subcutaneously administered. Then, the mice were observed for 30 minutes to investigate whether clonic convulsion was developed or not. To control mice, 0.5% methylcellulose solution was administered, and the same test was done. The results are shown in Table 12. The results are represented as the number of mice with no convulsion, per 5 mice. The present test was deemed to succeed when 4 mice among 5 mice in the control group developed convulsions.

TABLE 12

| Example | Dose | | |
| --- | --- | --- | --- |
| | 100 mg/kg | 50 mg/kg | 25 mg/kg |
| 1 | 4 | 2 | 2 |
| 2 | 5 | 3 | 2 |
| 3 | 5 | 3 | 2 |
| 4 | 5 | 4 | 2 |
| 5 | 4 | 1 | 1 |
| 6 | 5 | 2 | 1 |
| 7 | 4 | — | — |
| 8 | 5 | 2 | 0 |
| 9 | 5 | — | — |
| 10 | 3 | — | — |
| 11 | 4 | 1 | 3 |
| 12 | 5 | 3 | 1 |

TABLE 12-continued

| Example | Dose | | |
| --- | --- | --- | --- |
| | 100 mg/kg | 50 mg/kg | 25 mg/kg |
| 13 | 5 | 4 | 2 |
| 14 | 5 | 5 | 2 |
| 15 | 5 | 3 | 1 |
| 16 | 5 | 2 | 3 |
| 17 | 4 | 4 | 0 |
| 18 | 5 | 3 | 2 |
| 19 | 4 | 2 | 2 |
| 20 | 5 | 3 | 1 |
| 21 | 3 | — | — |
| 22 | 3 | — | — |
| 23 | 2 | — | — |
| 24 | 5 | 3 | 0 |
| 25 | — | 5 | 4 |
| 26 | — | 2 | 2 |
| 27 | — | 5 | 2 |
| 28 | — | 5 | 3 |
| 29 | — | 4 | 2 |
| 30 | — | 3 | 3 |
| 31 | 5 | 5 | 3 |
| 32 | 5 | 5 | 1 |

—: No test

As shown in Table 12, the compounds of the present invention exhibited anticonvulsant action in the present evaluation wherein the present compounds were orally administered to the model produced by subcutaneous injection of pentetrazol (minimum convulsion model, scPTZ). As for the compounds of Examples 11, 16, 25, 28, 30, and 31, more than half of the animals in each example exhibited anticonvulsant action even in 25 mg/kg oral administration.

Test 2: Rotarod Performance Test

The present test is a test for evaluating whether the test compound may disturb coordinated movement or not. Rotarod is an apparatus equipped with a rotating columnar bar whose diameter is 4 cm, in which a mouse is made to walk on the rotating bar, and the coordinated movement is evaluated from the result of walking (can walk or cannot walk). Slc: ddy male mice (purchased from Japan SLC, Inc., body weight: 20-30 g) were trained 3 hours before the test starts so that they could walk on a rotarod apparatus rotating with a speed of 12 rotations per minute for 5 minutes without falling. Only the mice which can walk in the training are used in the test. The test compound was orally administered to a group consisting of 5 mice. One hour after the administration, the mice were put on the rotarod apparatus rotating with a speed of 15 rotations per minute, and their walking performances were observed for 180 seconds and the time of walking was measured. To control mice, 0.5% methylcellulose solution was administered as test compound, and the same test was also done. The coordinated movement was evaluated with the average of the five mice's walking time (second). The results are shown in Table 13. The control group walked for 180 seconds.

TABLE 13

| Example | Dose | | |
| --- | --- | --- | --- |
| | 100 mg/kg | 50 mg/kg | 25 mg/kg |
| 1 | 180 | — | — |
| 2 | 180 | — | — |
| 3 | 180 | — | — |
| 4 | 180 | — | — |
| 5 | 180 | — | — |
| 6 | 180 | — | — |
| 7 | 180 | — | — |

TABLE 13-continued

| Example | Dose | | |
|---|---|---|---|
| | 100 mg/kg | 50 mg/kg | 25 mg/kg |
| 8 | 180 | — | — |
| 9 | 180 | — | — |
| 10 | 180 | — | — |
| 11 | 180 | — | — |
| 12 | 180 | — | — |
| 13 | 180 | — | — |
| 14 | 180 | — | — |
| 15 | 180 | — | — |
| 16 | 180 | — | — |
| 17 | 180 | — | — |
| 18 | 180 | — | — |
| 19 | 180 | — | — |
| 20 | 180 | — | — |
| 21 | 180 | — | — |
| 22 | 180 | — | — |
| 23 | 180 | — | — |
| 24 | 180 | — | — |
| 25 | — | 144.8 | 180 |
| 26 | — | 180 | — |
| 27 | — | 180 | — |
| 28 | — | 180 | — |
| 29 | — | 146.4 | 180 |
| 30 | — | 180 | — |
| 31 | 0 | 53.2 | 180 |
| 32 | 65.3 | 180 | — |

—: No test

As shown in Table 13, in the results of all Examples, mice receiving oral administration of 25 mg/kg or more walked on the rotarod apparatus without falling for 180 seconds, which means that all Examples did not disturb coordinated movement. Thus, the Example compounds evaluated with the model produced by subcutaneous injection of pentetrazol (minimum convulsion model, scPTZ) in Test 1 showed anticonvulsant action, but Test 2 demonstrated that the doses in Test 1 hardly disturbed coordinated movement.

Test 3: Evaluation of Anticonvulsant Effect in Mouse Model of Dravet Syndrome with Febrile Seizures This is a test for evaluating the anticonvulsant effect for febrile seizures of the test compounds in a mouse model of Dravet syndrome. In this test, BALB/c-Scn1a<+/−> mice were used (catalog number: RBRC06422; they are available from RIKEN BioResource Research Center via the National BioResource Project). The present mouse model having a mutation in a responsible gene for Dravet syndrome, Scn1A, presents with symptoms similar to febrile seizures caused by hyperthermia which is a symptom in a patient suffering from Dravet syndrome, and can be used as an animal model of spontaneous Dravet syndrome (for reference: the Japan Epilepsy Research Foundation, Annual Report 2015: 26: 69-76). To male mice model of Dravet syndrome (one group: 5-8 mice, body weight: 20-30 g) were orally administered the test compound. 50 minutes later, the mice were put in a chamber warmed with hot bath to evoke hyperthermia, and observed about the development of febrile seizures. Immediately after febrile seizure was developed, the rectal temperature was measured and used as the threshold body temperature for inducing febrile seizures. To control mice, 0.5% methylcellulose solution was administered as test compound, and the same test was also done. The anticonvulsant effect of the present test was evaluated with the dose needed to raise the threshold body temperature for inducing febrile seizures significantly compared with the control group, and the difference of the threshold body temperature for inducing febrile seizures from that of the control group. The results are shown in Table 14.

TABLE 14

| Example | Dose for anticonvulsive effect (mg/kg) | Difference of the threshold temperature of convulsion from that of the control group (° C.) |
|---|---|---|
| 2 | 50 | 0.6 |
| 3 | 100 | 0.7 |
| 13 | 50 | 0.6 |
| 20 | 100 | 0.6 |
| 25 | 12.5 | 0.3 |
| 29 | 25 | 0.7 |
| 31 | 12.5 | 0.3 |
| 32 | 25 | 0.5 |

As shown in Table 14, the compounds of the present invention exhibited some effect for raising the threshold temperature of seizure in mouse model of Dravet syndrome with febrile seizures, and thus, the result shows that the compounds of the present invention have anticonvulsant effect for Dravet model. In all the example compounds, the anticonvulsant effect for Dravet model was exhibited within the dose which did not disturb coordinated movement in Test 2: Rotarod performance test.

Test 4: Evaluation of the Potentiating Effect on GABA(A) Receptors

Using GABA(A) receptor expressing cells prepared according to Guideline for Generation of Stable Cell Lines (website of Lonza Japan; Non-patent Literature 4), the present test is done for evaluating the potentiating effect of a drug on GABA(A) receptors based on the electric current raised by GABA. The GABA(A) receptor expressing cells were used in electrophysiological study, wherein the electric current was measured when 2 μM GABA solution and then a mixture of 2 μM GABA and the test compound were added to the cells. The potentiating effect on GABA(A) receptors was evaluated on the basis of the increased current rate from the electric current generated by only 2 μM GABA to the electric current generated by the mixture of 2 μM GABA and the test compound, and the concentration of the test compound which exhibits 20% increase was shown as EC20. In addition, the electric current generated by a mixture of 2 μM GABA solution and the test compound with 10 μM flumazenil was measured, and the inhibition rate for the electric current by adding flumazenil was calculated compared to the electric current obtained in the absence of flumazenil. The results are shown in Table 15.

TABLE 15

| Example | The potentiating effect on GABA(A) receptors EC20 (μM) | Inhibition rate to the increased electric current by adding flumazenil (%) |
|---|---|---|
| 1 | 55 | — |
| 2 | 29 | <0 |
| 3 | 29 | <0 |
| 4 | >100 | — |
| 5 | >300 | — |
| 6 | 3.3 | — |
| 7 | 5.4 | — |
| 8 | 3.2 | — |
| 9 | 2.7 | — |
| 10 | 247 | — |
| 11 | 5.1 | — |
| 12 | 234 | — |
| 13 | 71 | <0 |
| 14 | 32 | — |
| 15 | >300 | — |
| 16 | >300 | — |

TABLE 15-continued

| Example | The potentiating effect on GABA(A) receptors EC20 (μM) | Inhibition rate to the increased electric current by adding flumazenil (%) |
|---|---|---|
| 17 | 45 | — |
| 18 | 37 | <0 |
| 19 | 34 | — |
| 20 | 20 | 55 |
| 21 | 9.6 | — |
| 22 | >300 | — |
| 23 | 190 | — |
| 24 | 86 | — |
| 25 | 16 | 12 |
| 26 | >100 | — |
| 27 | 39 | <0 |
| 28 | 9.3 | 24 |
| 29 | 1.1 | 7 |
| 31 | 15 | <0 |
| 32 | 3.6 | <0 |
| clobazam | 0.34 | 88 |
| diazepam | 0.03 | 93 |

—: unevaluated

As shown in Table 15, the present compounds showed the potentiating effect on GABA(A) receptors. The potentiating effects of clobazam and diazepam which are classified as benzodiazepines on GABA(A) receptors were strongly inhibited with flumazenil which is a benzodiazepine antagonist, while the potentiating effect of the present compounds on GABA(A) receptors was very weakly inhibited with flumazenil, which suggested that the potentiating effect of the present compounds on GABA(A) receptors can arise by a different mechanism from benzodiazepines.

Test 5: Evaluation of Antidepressant Effect in Rat Forced Swimming Test

The present test can evaluate antidepressant effect of a drug. When a rat is thrown into a water bath from which the rat cannot escape to be made to swim, the rat takes on escape behavior in the beginning and then becomes immobile. Next day, when the rat is thrown into a water bath again, the immobility appears earlier than that of the first trial. The method can evaluate the antidepressant effect of a test compound by using the duration of the immobility time as an indicator of depressive behavior. A day before the test, male Wister strain rats (purchased from Charles River Laboratories Japan, body weight: 260-300 g) were made to swim in a water bath for 15 minutes. On the test day, the test compound was orally administered to the rats (10-12 rats in one group). An hour later, the rats were made to swim again for 5 minutes and each immobility time was measured. In the control group, 0.5% methylcellulose solution as the test compound was administered to the rats which were subjected to the same behavior test. The antidepressant effect was indicated by the average rate of deceasing the immobility time per that of the control group. The results are shown in Table 16.

TABLE 16

| | Dose | | |
|---|---|---|---|
| Example | 3 mg/kg | 10 mg/kg | 30 mg/kg |
| 29 | 12.3 | 29.4* | — |
| 32 | 25.3* | 31.6* | 58.9* |
| diazepam | — | 18.3 | — |

—: unevaluated,
*showing statistically significant difference

As shown in Table 16, Examples 29 and 32 significantly decreased the immobility time of rat forced swimming models, which suggests that these compounds have antidepressant effect. On the other hand, diazepam did not show antidepressant effect in the rat forced swimming test though Test 4 showed that diazepam has the potentiating effect on GABA(A) receptors as with the present compounds. Diazepam is one of benzodiazepines, which is used as an anticonvulsant drug. The present result that the present compounds exhibited the effect in the model to which benzodiazepines did not exhibit the effect, suggests that the mechanism of the present compounds about the potentiating effect on GABA(A) receptors is different from that of benzodiazepines as shown in Test 4, and an unknown mechanism which the present compounds have can show an antidepressant effect which benzodiazepines do not have. Thus, it was suggested that the present compounds can have therapeutic or preventive effect for not only epileptic seizure, but also depressive symptom with which patients suffering from epilepsy are accompanied at a high rate.

As shown above, the present compounds exhibited potent anticonvulsant action in the test with a model produced by subcutaneous injection of pentetrazol (minimum convulsion model, scPTZ). In a mouse model of Dravet syndrome which is known as a refractory generalized epilepsy and whose responsible mutated gene is identified, it was demonstrated that the present compounds could raise the threshold body temperature for inducing febrile seizures in the dose which did not disturb coordinated movement. Thus, the present compounds are useful as an antiepileptic drug, i.e., a medicament for treating and/or preventing generalized seizure including tonic seizure, clonic seizure, absence seizure, myoclonic seizure, and atonic seizure; focal seizure; an unknown seizure; and generalized seizure including Dravet syndrome, West syndrome, and Lennox-Gastaut syndrome which belong to refractory epilepsy to medical therapy. The present compounds also have the potentiating effect on GABA(A) receptors, and thereby the present compounds are also useful as a medicament for treating and/or preventing anxiety disorders, obsessive-compulsive disorder, REM sleep behavior disorder associated with Parkinson's disease/dementia with Lewy bodies, which can be treated with existing GABA(A) receptor agonists. The potentiating effect of the present compounds on GABA(A) receptors is exerted in a different mechanism of action from benzodiazepine which is one of existing agonists of GABAergic neurons, i.e., the present compounds exhibited the antidepressant effect in rat forced swimming test to which benzodiazepine does not exhibit the effect, thus the present compounds are expected to have some effect for depressive symptom accompanying or unaccompanying epilepsy, be useful as a medicament for treating and/or preventing depressive syndrome and the like, and also have utility which existing antiepileptic drugs do not have. In addition, the present compounds are expected to improve the pathological conditions of developmental disorder, autism, bipolar disorder and its related disorders, schizophrenia spectrum disorder, Alzheimer's disease and the other neurocognitive disorders, amyotrophic lateral sclerosis, and Parkinson's disease, which have underlying reason for the dysfunction of GABAergic system.

INDUSTRIAL APPLICABILITY

The compounds of the present invention have a potent anticonvulsant effect as well as the potentiating effect on GABA(A) receptors, thus the present compounds are useful as a medicament for treating and/or preventing diseases associated with hypofunction of GABAergic system. In addition, the present compounds have an effect for enhancing inhibition (I) in balance of excitation (E) and inhibition (I) (E/I balance), thus the present compounds are useful as a medicament for treating and/or preventing a disease in which E is increased and/or I is decreased in E/I balance.

The invention claimed is:

1. A compound or a pharmaceutically acceptable salt thereof, wherein the compound is selected from the group consisting of:
   a) 2-[3-(4-chlorophenyl)-1,2,4-oxadiazol-5-yl]-2-methylpropanamide,
   b) 2-[5-(4-chlorophenyl)-1,2,4-oxadiazol-3-yl]-2-methylpropanamide,
   c) 5-[3-(4-fluorophenyl)-1,2,4-oxadiazol-5-yl]-1-methylpyrrolidin-2-one,
   d) 5-[3-(4-chlorophenyl)-1,2,4-oxadiazol-5-yl]-1-methylpyrrolidin-2-one,
   e) (S)-5-[3-(4-fluorophenyl)-1,2,4-oxadiazol-5-yl]-1-methylpyrrolidin-2-one, and
   f) (R)-5-[3-(4-fluorophenyl)-1,2,4-oxadiazol-5-yl]-1-methylpyrrolidin-2-one.

2. The compound or a pharmaceutically acceptable salt thereof according to claim 1, wherein the compound is 5-[3-(4-fluorophenyl)-1,2,4-oxadiazol-5-yl]-1-methylpyrrolidin-2-one.

3. The compound or a pharmaceutically acceptable salt thereof according to claim 1, wherein the compound is (S)-5-[3-(4-fluorophenyl)-1,2,4-oxadiazol-5-yl]-1-methylpyrrolidin-2-one.

4. The compound or a pharmaceutically acceptable salt thereof according to claim 1, wherein the compound is (R)-5-[3-(4-fluorophenyl)-1,2,4-oxadiazol-5-yl]-1-methylpyrrolidin-2-one.

5. A pharmaceutical composition, comprising:
   a compound or a pharmaceutically acceptable salt thereof; and
   a pharmaceutically acceptable additive agent,
   wherein the compound is selected from the group consisting of:
   a) 2-[3-(4-chlorophenyl)-1,2,4-oxadiazol-5-yl]-2-methylpropanamide,
   b) 2-[5-(4-chlorophenyl)-1,2,4-oxadiazol-3-yl]-2-methylpropanamide,
   c) 5-[3-(4-fluorophenyl)-1,2,4-oxadiazol-5-yl]-1-methylpyrrolidin-2-one,
   d) 5-[3-(4-chlorophenyl)-1,2,4-oxadiazol-5-yl]-1-methylpyrrolidin-2-one,
   e) (S)-5-[3-(4-fluorophenyl)-1,2,4-oxadiazol-5-yl]-1-methylpyrrolidin-2-one, and
   f) (R)-5-[3-(4-fluorophenyl)-1,2,4-oxadiazol-5-yl]-1-methylpyrrolidin-2-one.

6. The pharmaceutical composition of claim 5, wherein the compound is 5-[3-(4-fluorophenyl)-1,2,4-oxadiazol-5-yl]-1-methylpyrrolidin-2-one.

7. The pharmaceutical composition of claim 5, wherein the compound is (S)-5-[3-(4-fluorophenyl)-1,2,4-oxadiazol-5-yl]-1-methylpyrrolidin-2-one.

8. The pharmaceutical composition of claim 5, wherein the compound is (R)-5-[3-(4-fluorophenyl)-1,2,4-oxadiazol-5-yl]-1-methylpyrrolidin-2-one.

9. A method for treating a disease selected from the group consisting of epilepsy, depressive syndrome, anxiety disorders, and bipolar disorder and its related disorders, comprising:
administering to a patient in need thereof a therapeutically effective amount of the compound or a pharmaceutically acceptable salt thereof according to claim 1.

10. The method of claim 9, wherein the compound is 5-[3-(4-fluorophenyl)-1,2,4-oxadiazol-5-yl]-1-methylpyrrolidin-2-one.

11. The method of claim 9, wherein the compound is (S)-5-[3-(4-fluorophenyl)-1,2,4-oxadiazol-5-yl]-1-methylpyrrolidin-2-one.

12. The method of claim 9, wherein the compound is (R)-5-[3-(4-fluorophenyl)-1,2,4-oxadiazol-5-yl]-1-methylpyrrolidin-2-one.

13. The method of claim 9, wherein the disease is Dravet syndrome, Lennox-Gastaut syndrome, epileptic seizure (tonic seizure, clonic seizure, absence seizure, myoclonic seizure, generalized seizure including atonic seizure, focal seizure, an unknown seizure), status epilepticus, Angelman syndrome, West syndrome, tuberous sclerosis, depression/major depressive disorder, social anxiety disorder, panic disorder, panic attack, agoraphobia, generalized anxiety disorder, depressive symptom associated with bipolar and related disorders, depressive state associated with bipolar and related disorders, or anxiety symptom associated with bipolar and related disorders.

14. The method of claim 13, wherein the compound is 5-[3-(4-fluorophenyl)-1,2,4-oxadiazol-5-yl]-1-methylpyrrolidin-2-one.

15. The method of claim 13, wherein the compound is (S)-5-[3-(4-fluorophenyl)-1,2,4-oxadiazol-5-yl]-1-methylpyrrolidin-2-one.

16. The method of claim 13, wherein the compound is (R)-5-[3-(4-fluorophenyl)-1,2,4-oxadiazol-5-yl]-1-methylpyrrolidin-2-one.

17. The method of claim 13, wherein the disease is epileptic seizure, status epilepticus, Angelman syndrome, West syndrome, or tuberous sclerosis, and the compound is 5-[3-(4-fluorophenyl)-1,2,4-oxadiazol-5-yl]-1-methylpyrrolidin-2-one.

18. The method of claim 13, wherein the disease is epileptic seizure, status epilepticus, Angelman syndrome, West syndrome, or tuberous sclerosis, and the compound is (S)-5-[3-(4-fluorophenyl)-1,2,4-oxadiazol-5-yl]-1-methylpyrrolidin-2-one.

19. The method of claim 13, wherein the disease is epileptic seizure, status epilepticus, Angelman syndrome, West syndrome, or tuberous sclerosis, and the compound is (R)-5-[3-(4-fluorophenyl)-1,2,4-oxadiazol-5-yl]-1-methylpyrrolidin-2-one.

20. The method of claim 13, wherein the disease is depression/major depressive disorder, and the compound is 5-[3-(4-fluorophenyl)-1,2,4-oxadiazol-5-yl]-1-methylpyrrolidin-2-one.

21. The method of claim 13, wherein the disease is depression/major depressive disorder, and the compound is (S)-5-[3-(4-fluorophenyl)-1,2,4-oxadiazol-5-yl]-1-methylpyrrolidin-2-one.

22. The method of claim 13, wherein the disease is depression/major depressive disorder, and the compound is (R)-5-[3-(4-fluorophenyl)-1,2,4-oxadiazol-5-yl]-1-methylpyrrolidin-2-one.

23. The method of claim 13, wherein the disease is social anxiety disorder, panic disorder, panic attack, agoraphobia, or generalized anxiety disorder, and the compound is 5-[3-(4-fluorophenyl)-1,2,4-oxadiazol-5-yl]-1-methylpyrrolidin-2-one.

24. The method of claim 13, wherein the disease is social anxiety disorder, panic disorder, panic attack, agoraphobia, or generalized anxiety disorder, and the compound is (S)-5-[3-(4-fluorophenyl)-1,2,4-oxadiazol-5-yl]-1-methylpyrrolidin-2-one.

25. The method of claim 13, wherein the disease is social anxiety disorder, panic disorder, panic attack, agoraphobia, or generalized anxiety disorder, and the compound is (R)-5-[3-(4-fluorophenyl)-1,2,4-oxadiazol-5-yl]-1-methylpyrrolidin-2-one.

26. The method of claim 13, wherein the disease is depressive symptom associated with bipolar and related disorders, depressive state associated with bipolar and related disorders, or anxiety symptom associated with bipolar and related disorders, and the compound is 5-[3-(4-fluorophenyl)-1,2,4-oxadiazol-5-yl]-1-methylpyrrolidin-2-one.

27. The method of claim 13, wherein the disease is depressive symptom associated with bipolar and related disorders, depressive state associated with bipolar and related disorders, or anxiety symptom associated with bipolar and related disorders, and the compound is (S)-5-[3-(4-fluorophenyl)-1,2,4-oxadiazol-5-yl]-1-methylpyrrolidin-2-one.

28. The method of claim 13, wherein the disease is depressive symptom associated with bipolar and related disorders, depressive state associated with bipolar and related disorders, or anxiety symptom associated with bipolar and related disorders, and the compound is (R)-5-[3-(4-fluorophenyl)-1,2,4-oxadiazol-5-yl]-1-methylpyrrolidin-2-one.

29. The method of claim 13, wherein the disease is tonic seizure, clonic seizure, absence seizure, myoclonic seizure, generalized seizure including atonic seizure, focal seizure, or an unknown seizure, and the compound is 5-[3-(4-fluorophenyl)-1,2,4-oxadiazol-5-yl]-1-methylpyrrolidin-2-one, (S)-5-[3-(4-fluorophenyl)-1,2,4-oxadiazol-5-yl]-1-methylpyrrolidin-2-one or (R)-5-[3-(4-fluorophenyl)-1,2,4-oxadiazol-5-yl]-1-methylpyrrolidin-2-one.

30. The method of claim 13, wherein the disease is tonic seizure, clonic seizure, absence seizure, myoclonic seizure, generalized seizure including atonic seizure, focal seizure, or an unknown seizure, and the compound is (S)-5-[3-(4-fluorophenyl)-1,2,4-oxadiazol-5-yl]-1-methylpyrrolidin-2-one.

\* \* \* \* \*